(12) United States Patent
Cataldo et al.

(10) Patent No.: US 9,993,487 B2
(45) Date of Patent: Jun. 12, 2018

(54) CYCLODEXTRIN AND BUDESONIDE DERIVATIVE COMPOSITIONS AND METHODS

(71) Applicants: Universite de Liege, Angleur (BE); Paul Maes, Vise (BE)

(72) Inventors: Didier Cataldo, Olne (BE); Brigitte Evrard, Embourg (BE); Gilles Dufour, Wanze (BE); Pascal de Tullio, Jupille-sur-Meuse (BE); Paul Maes, Vise (BE)

(*) Notice: Subject to any disclaimer, the term of this patent is extended or adjusted under 35 U.S.C. 154(b) by 0 days. days.

(21) Appl. No.: 14/672,831

(22) Filed: Mar. 30, 2015

(65) Prior Publication Data
US 2016/0051568 A1 Feb. 25, 2016

Related U.S. Application Data

(60) Provisional application No. 61/972,209, filed on Mar. 28, 2014.

(30) Foreign Application Priority Data

Mar. 28, 2014 (EP) .................................. 14162158

(51) Int. Cl.
| | | |
|---|---|---|
| A61K 31/58 | (2006.01) | |
| A61K 31/56 | (2006.01) | |
| A61K 31/573 | (2006.01) | |
| C08B 37/16 | (2006.01) | |
| C08L 5/16 | (2006.01) | |
| A61K 9/00 | (2006.01) | |
| A61K 31/57 | (2006.01) | |
| A61K 47/40 | (2006.01) | |
| A61K 47/69 | (2017.01) | |

(52) U.S. Cl.
CPC ............ *A61K 31/58* (2013.01); *A61K 9/0073* (2013.01); *A61K 31/56* (2013.01); *A61K 31/57* (2013.01); *A61K 31/573* (2013.01); *A61K 47/40* (2013.01); *A61K 47/6951* (2017.08); *C08B 37/0015* (2013.01); *C08L 5/16* (2013.01)

(58) Field of Classification Search
CPC ....................................................... A61K 31/58
See application file for complete search history.

(56) References Cited

U.S. PATENT DOCUMENTS

2009/0312724 A1 12/2009 Pipkin et al.
2013/0196947 A1 8/2013 Cataldo et al.

FOREIGN PATENT DOCUMENTS

| EP | 1894559 A1 | 3/2008 | |
|---|---|---|---|
| WO | WO-05065649 A1 | 7/2005 | |
| WO | WO 2007075800 A2 * | 7/2007 | ........... A61K 9/0078 |
| WO | 2015109201 | 7/2015 | |

OTHER PUBLICATIONS

Mayo Clinic. "COPD." © 2015. Available from: < http://www.mayoclinic.org/diseases-conditions/copd/basics/treatment/con-20032017?p=1 >.*
"Inflammation in COPD." (c) 2012. Available from: < http://www.thinkcopdifferently.com/en/Think-COPDifferently/Inflammation-in-COPD >.*
Mayo Clinic. "COPD." © 2015. pp. 6-7 of 10. Available from: < http://www.mayoclinic.org/diseases-conditions/copd/basics/treatment/con-20032017?p=1 >.*
Williams, E., et al. "budesonide (oral inhalation, Pulmicort, Pulmicort Flexhaler." © 2015. Available from: < http://www.medicinenet.com/budesonide_inhaler/article.htm.*
Pharma Models. © 2017. Available from: < http://www.pharmamodels.net/indications/inflammatory-lung-diseases/ >.*
Mayo Clinic. "Pulmonary fibrosis." © 2017. Available from: < http://www.mayoclinic.org/diseases-conditions/pulmonary-fibrosis/home/ovc-20211752 >.*
Agüeros et al., Simultaneous quantification of different cyclodextrins and Gantrez by HPLC with evaporative light scattering detection. J Pharm Biomed Anal. Sep. 15, 2005;39(3-4):495-502.
Cataldo et al., Matrix metalloproteinase-9 deficiency impairs cellular infiltration and bronchial hyperresponsiveness during allergen-induced airway inflammation. Am J Pathol. Aug. 2002;161(2):491-8.
Connors. The Stability of Cyclodextrin Complexes in Solution. Chem Rev. Aug. 5, 1997;97(5):1325-1358.
Culpitt et al., Effect of high dose inhaled steroid on cells, cytokines, and proteases in induced; sputum in chronic obstructive pulmonary disease. Am J Respir Crit Care Med. Nov. 1999;160(5 Pt 1):1635-9.
Djedaini et al., Nuclear magnetic resonance investigation of the stoichiometries in beta-cyclodextrin:steroid inclusion complexes. J Pharm Sci. Dec. 1991;80(12):1157-1161.
Ford et al., Human parainfluenza type 3 virus impairs the efficacy of glucocorticoids to limit allergy-induced pulmonary inflammation in guinea-pigs. Clin Sci (Lond). Nov. 2013;125(10):471-482.
Loftsson et al., Pharmaceutical applications of cyclodextrins: basic science and product development. J Pharm Pharmacol. Nov. 2010;62(11):1607-21.
Synwoldt, Improvement of animal models of COPD and identification of new therapeutic intervention principle therein. Univeristat Konstanz. Jul. 31, 2012;1-133.

(Continued)

*Primary Examiner* — Noble E Jarrell
*Assistant Examiner* — John S Kenyon
(74) *Attorney, Agent, or Firm* — Lewis Brisbois Bisgaard & Smith LLP; Peter Manso, Esq.

(57) ABSTRACT

The present invention relates to novel and useful pharmaceutical compositions formulated with a cyclodextrin compound and a budesonide derivative for the treatment and/or prevention of pulmonary inflammatory disease. The present invention also relates to a novel and useful analytical technique for the detection and the quantification of HP-β-CD in solution. More specifically, the present invention relates to the use of a validated 1H NMR analysis for the detection and quantification of cyclodextrins directly in pharmaceutical formulations without any extraction or separation steps for liquid formulations.

30 Claims, 14 Drawing Sheets

(56) References Cited

OTHER PUBLICATIONS

Szejtli. Cyclodextrin Technology, Kluwer Academic Publishers 1998, pp. 1-78.
Szeman et al., High-performance liquid chromatographic determination of 2-hydroxypropyl-gamma-cyclodextrin in different biological fluids based on cyclodextrin enhanced fluorescence. J Chromatogr B Analyt Technol Biomed Life Sci. Jul. 15, 2002;774(2):157-64.
Thompson. Cyclodextrins—enabling excipients: their present and future use in pharmaceuticals. Crit Rev Ther Drug Carrier Syst. 1997;14(1):1-104.
Vogt et al., 2D solid-state Nmr analysis of inclusion in drug-cyclodextrin complexes. Mol Pharm. Nov. 5, 2012;9(11):3357-74.
Williams et al., Modulation of ozone-induced airway hyper-responsiveness and inflammation by interleukin-13. Eur Respir J. Sep. 2008;32(3):571-578.
Wu Xiao et al., Pulmonary and nasal anti-inflammatory and anti-allergy inhalation aerosol delivery systems. Anti-Inflammatory and Anti-Allergy Agents in Medical Chemistry. Jun. 2011; 10(3):215-229.
Vozone, C.M and Marques, H.M.C., Complexation of Budesonide in Cyclodextrins and Particle Aerodynameic Characterization of the complex Solid Form for Dry Powder Inhalation. Journal of Inclusion Phenomena and Macrocyclic Chemistry, Dec. 31, 2002, vol. 44, No. 1-4, pp. 111-116.

* cited by examiner

CYCLODEXTRIN AND BUDESONIDE DERIVATIVE COMPOSITIONS AND METHODS

RELATED APPLICATIONS

This application for U.S. patent relates to and incorporates herein by reference in their entireties, as if fully set forth herein, U.S. Provisional Application No. 61/972,209, filed on 28 Mar. 2014 and entitled "Compositions of Cyclodextrin with Budesonide Derivatives and Methods" and European Application No. EP14132158 BE 28.03.2014, entitled "Composition of cyclodextrin with budesonide derivatives for treatment and prevention of pulmonary inflammatory disease", deposited by the Universitè de Liegè and assigned Publication No. EP14162158.1.

FIELD OF INVENTION

The present invention relates to novel and useful pharmaceutical compositions formulated with a cyclodextrin compound and a budesonide derivative for the treatment and/or prevention of pulmonary inflammatory disease. The present invention also relates to a novel and useful analytical technique for the detection and the quantification of HP-β-CD in solution. More specifically, the present invention relates to the use of a validated 1H NMR analysis for the detection and quantification of cyclodextrins directly in pharmaceutical formulations without any extraction or separation steps for liquid formulations.

BACKGROUND

Pulmonary inflammatory disease (PID) is a disease state characterized by airflow limitation that is not fully reversible. The airflow limitation is associated with an abnormal inflammatory response of the lungs to, for example, noxious particles (fine particles such as those found in smoke and haze, with a diameter of 2.5 micrometers or less).

Pulmonary inflammatory diseases comprise inflammatory asthma i.e. asthma at a severe stage, chronic obstructive disease (COPD) such as chronic bronchitis, obstructive bronchiolitis, emphysema, pulmonary fibrosis, cystic fibrosis, and the like.

In PID patients, there is a significant neutrophilic inflammation in the bronchial walls leading to progressive destruction of airways structures by the repeated productions of proteases and oxidants (oxygen reactive species). To date, marketed therapies are not able to adequately decrease or prevent this neutrophilic inflammation in PID patients. In particular, it is well know that inhaled or oral steroids display no efficiency against neutrophilic inflammation. For example, in a study conducted by S. Culpitt et al.: Am J Respir Crit Care Med. 160: 1635-1639 (1999), which was performed in COPD patients, it reports the lack of efficacy of high doses inhaled steroids in COPD-related neutrophilic inflammation and chemotactic agents for neutrophils (mainly IL-8 in humans).

In view of the ineffectiveness of current steroidal treatment in PID patients, there is a need for effective steroidal treatment to adequately decrease or prevent neutrophilic inflammation in PID patients.

SUMMARY OF THE INVENTION

In brief, the present invention overcomes the above-mentioned shortcomings and disadvantages associated with the current use of steroidal therapy in PID patients through the discovery of new, and useful pharmaceutical compositions for effective use in the therapeutic treatment and/or prevention of pulmonary inflammatory diseases in a host mammal in need of such treatment.

Generally speaking, the present invention relates to novel and useful pharmaceutical compositions formulated with a cyclodextrin compound and a budesonide derivative for the treatment and/or prevention of pulmonary inflammatory disease. The present invention also relates to a novel and useful analytical technique for the detection and the quantification of HP-β-CD in solution. More specifically, the present invention relates to the use of a validated 1H NMR analysis for the detection and quantification of cyclodextrins directly in pharmaceutical formulations without any extraction or separation steps for liquid formulations.

The novel compositions and methods of the present invention comprise compositions formulated with a cyclodextrin compound and a budesonide derivative of formula (I):

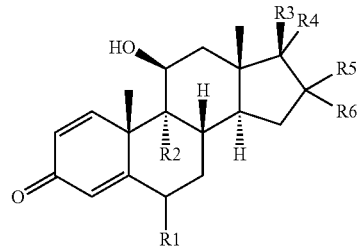

and uses thereof to treat and/or prevent PID in host mammals in need of such treatment, wherein "R1" and "R2" each independently represent a hydrogen atom, a halogen, $C_{1-5}$-alkyl, $C_{3-8}$-cycloalkyl, hydroxy, $C_{1-5}$-alkoxy, $C_{1-5}$-alkoxy, $C_{1-5}$-alkyl, $C_{1-5}$-alkyl optionally mono- or polysubstituted with a halogen atom, $C_{1-5}$-alkoxycarbonyl or $C_{1-5}$-alkoxycarbonyl-$C_{1-6}$-alkyl;

"R3", "R4", "R5" and "R6" each independently represent hydrogen, a hydroxyl moiety, $C_{1-5}$-alkoxy, $C_{1-5}$-alkoxycarbonyl, hydroxycarbonyl, $C_{1-5}$-alkylcarbonyl optionally mono- or polysubstituted with a halogen atom, $C_{1-5}$-alkylcarbonyloxy, $C_{3-8}$-cycloalkylcarbonyloxy, $C_{1-5}$alkyl thio, $C_{1-5}$alkyl sulfonyl, $C_{1-5}$-alkylsulfinyl, furan, furan carbonyloxy, $C_{1-5}$-alkythiocarbonyl optionally mono- or polysubstituted with a halogen atom or propionyloxymethylcarbonyl;

"R4" and "R5" optionally form together a hydrocarbon ring of 3 to 5 atoms, two carbon atoms optionally being replaced by an oxygen atom and the ring being optionally substituted by a $C_{1-5}$-alkyl group. For example, bis-oxy hydrocarbon ring of 3 to 5 atoms, with two carbon atoms being replaced by an oxygen atom, and optionally substituted by an alkyl group such as a propyl group; or a salt thereof with a pharmaceutically acceptable acid or base, or any optical isomer or mixture of optical isomers, including a racemic mixture or any tautomeric form thereof for use in the therapeutic and/or prevention treatment of pulmonary inflammatory disease in a host mammal in need of such treatment.

By "$C_{1-5}$-alkyl", as used herein, it means a straight or branched saturated or unsaturated hydrocarbon group with 1-5 carbon atoms such as methyl, propyl, butyl, isopentyl, 1-methylbutyl, 1,2-dimethylbutyl, 2-ethylbutyl and the like.

By "$C_{3-8}$-cycloalkyl", as used herein, it means a saturated or partially unsaturated hydrocarbyl group with 3 or more carbons in a ring, preferably from 3 to 8 carbon atoms. Examples of cycloalkyl group are cyclopropyl, cyclobutyl, cyclopentyl, cyclohexyl and the like.

By "$C_{1-5}$-alkoxy", also denoted as $C_{1-5}$-alkyloxy, as used herein, it means a straight or branched monovalent substituent comprising a $C_{1-5}$-alkyl group linked through an ether oxygen having its free valence bond from the ether oxygen and having 1 to 5 carbon atoms such as methoxy, ethoxy, propyloxy, isopropoxy, butyloxy, sec-butyloxy, ter-butyloxy, 2-methylbutoxy, pentyloxy and the like.

By "$C_{1-5}$-alkoxy-$C_{1-5}$-alkyl", as used herein, it means 2-10 carbon atoms interrupted by an oxygen atom such as —CH$_2$—O—CH$_3$, —CH$_2$CH$_2$O$^-$CH$_3$, $^-$CH$_2$$^-$O$^-$CH$_2$CH$_3$, $^-$CH$_2$$^-$O$^-$CH(CH$_3$)$_2$, CH$_2$CH$_2$$^-$O$^-$CH(CH$_3$)2-CH(CH$_3$) CH$_2$$^-$O$^-$CH$_3$ and the like.

By "$C_{1-5}$-alkylthio", whether alone or in combination, as used herein, it refers to a straight or branched monovalent substituent comprising a $C_{1-5}$-alkyl group linked through a divalent sulphur atom having its free valence bond from the sulphur atom and having 1 to 5 carbon atoms, such as methylthio, ethylthio, propylthio, isopropylthio, butylthio, pentylthio, 3-methylpentylthio and the like.

By "$C_{1-5}$-alkylsulfonyl", as used herein, it refers to a monovalent substituent comprising a $C_{1-5}$-alkyl group linked through a sulfonyl group (—S(═O)), such as methylsulfonyl, ethylsulfonyl, propylsulfonyl, isopropylsulfonyl, butylsulfonyl, pentylsulfonyl, 2-methylpentylsulfonyl and the like.

By "$C_{1-5}$-alkylsulfinyl", as used herein, it refers to a monovalent substituent comprising a $C_{1-5}$-alkyl group linked through a sulfinyl group (—S(═O)), such as methylsulfinyl, ethylsulfinyl, propylsulfinyl, isopropylsulfinyl, tert-butylsulfinyl, pentylsulfinyl, 2-ethylbutylsulfinyl and the like.

By "furan", as used herein, it means:

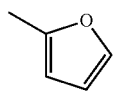

By "furan carbonyloxy", as used herein, it means:

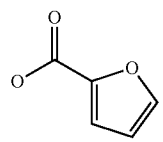

II

By "halogen", as used herein, it means fluorine, chlorine, bromine or iodine.

By "R4" and "R5", optionally they may form together a hydrocarbon ring of 3 to 5 atoms, of which two carbon atoms may optionally be replaced by an oxygen atom and the ring may optionally be substituted with a $C_{1-5}$ alkyl group, including for example, bis oxy hydrocarbon ring of 3 to 5 atoms, of which two carbon atom may be replaced with an oxygen atom, and may optionally be substituted with an alkyl group, such as 1,3-dioxolan-2-yl)propyl or

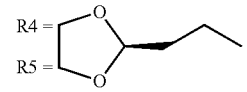

I

Preferred budesonide derivatives according to the invention are mometasone furoate or fluticasone furoate represented by the general formula (I) with a furane carbonyloxy group, respectively, in R3 or R4, as illustrated hereafter:

| Mometasone furoate | Fluticasone furoate |
|---|---|
| R1 = —H<br>R2 = Cl<br>R3 = (furan-2-carbonyloxy)<br>R4 = C(O)CH$_2$Cl<br>R5 = H<br>R6 = H | R1 = F<br>R2 = F<br>R3 = C(O)SCH$_2$F<br>R4 = (furan-2-carbonyloxy)<br>R5 =<br>R6 = —H |

Mometasone furoate is commercially available from Pfizer and Merck, whereas fluticasone furoate is commercially available from GSK.

Other preferred budesonide derivatives according to the present invention are fluticasone propionate or beclomethasone dipropionate represented by the general formula (I) with at least a propylcarbonyloxy group or propionate group in R4, as follows:

| Fluticasone propionate | Beclomethasone dipropionate |
|---|---|
| R1 = F<br>R2 = F<br>R3 = C(O)SCH$_2$F<br>R4 = propionyloxy<br>R5 =<br>R6 = —H | R1 = —H<br>R2 = Cl<br>R3 = C(O)CH$_2$O-propionyl<br>R4 = propionyloxy<br>R5 =<br>R6 = —H |

Fluticasone propionate is commercially available from GSK under the trade name Flixotide, and beclomethasone dipropionate is commercially available from UCB, SANDOZ, TEVA, and CHIESI under the trade name QVAR, Ecobec and Beclophar.

In accordance with the present invention, the most preferred budesonide derivative is budesonide. Budesonide is a corticosteroid and is represented by the general formula (I) wherein:

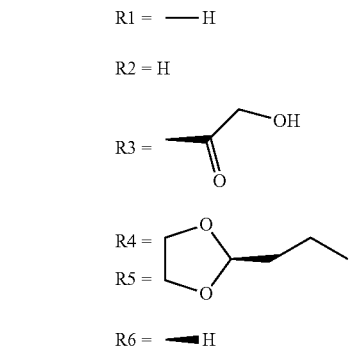

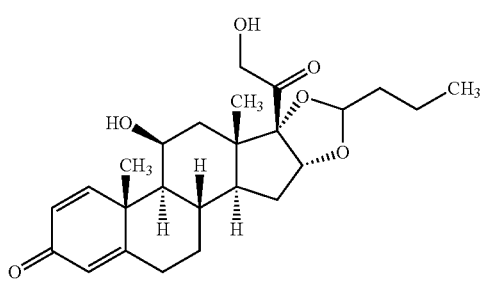

Budesonide, is also named (R,S)-11(3,16a,17,21-tetrahydroxypregna-1,4-diene-3,20-dione cyclic 16,17-acetal with butyraldehyde or 16,17-(butylidenebis(oxy))-11,21-dihydroxy-, (11-β3,16-a)-pregna-1,4-diene-3,20-dione. The chemical formula, molecular weight and CAS number for Budesonide are $C_{25}H_{34}O_6$ MW: 430.5 and 51333-22-3, respectively.

Budesonide is a racemate consisting of a mixture of the two diastereomers 22R and 22S and is provided commercially as a mixture of the two isomers (22R and 22S).

Commercial formulations of budesonide in solution are provided by AstraZeneca LP (Wilmington, Del.) under the trademarks, Pulmicort Respules®, Rhinocort® Aqua, Rhinocort® and in powder under the trademark Nasal Inhaler and Pulmicort® Turbuhaler, and under its generic name. Budesonide in powder form (raw material) is provided by Indis (Belgium).

Betamethsone is also contemplated by the present invention. Like budesonide, betamethasone is a corticosteroid and is represented by the general formula as follows:

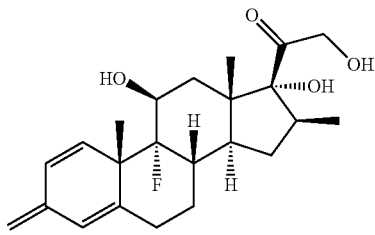

The IUPAC name for betamethasone is (8S,9R,10S,11S,13S,14S,16S,17R)-9-fluoro-11,17-dihydroxy-17-(2-hydroxyacetyl)-10,13,16-trimethyl-6,7,8,11,12,14,15,16-octahydrocyclopenta[a]phenanthren-3-one. The chemical formula, molecular weight and CAS ID number for Budesonide are C22H29F05, 392.461063 g/mol and 378-44-9, respectively.

Alternative chemical names for betamethasone include Celestone, Rinderon Betadexamethasone and Flubenisolone.

Fluticasone is another corticosteroid contemplated by the present invention and is represented by the general formula as follows:

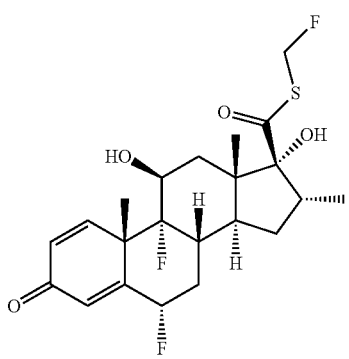

The IUPAC name for fluticasone is (6a,11(3,16a,17a)-6,9-difluoro-17-1{[(fluoromethyl)thio]carbonyl}-11-hydroxy-16-methyl-3-oxoandrosta-1,4-dien-17-yl 2-furancarboxylate. The chemical formula, molecular weight and CAS ID number for Fluticasone are $C_{27}H_{29}F_3O_6S$, 538.576 g/mol and 80474-14-2, respectively.

Cyclodextrins are known to be cyclic oligosaccharides produced by bacterial degradation from starch. Cyclodextrins are composed of 6, 7 or 8 a-D-glucopyranoside units and named accordingly a, 0 or y cyclodextrins.

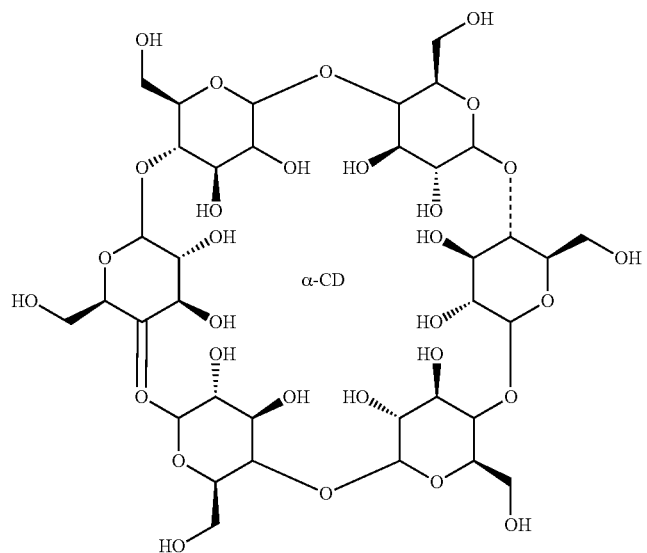
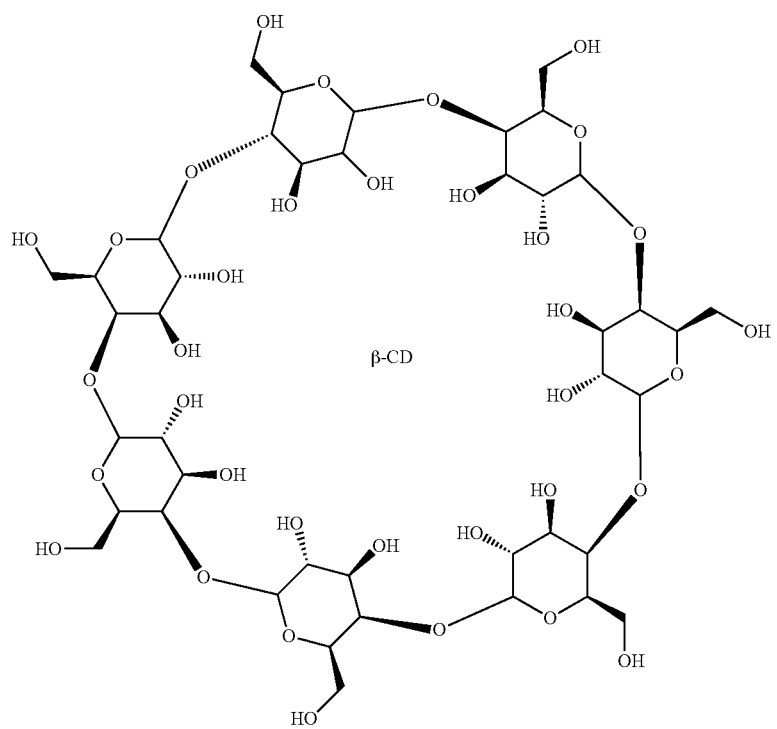

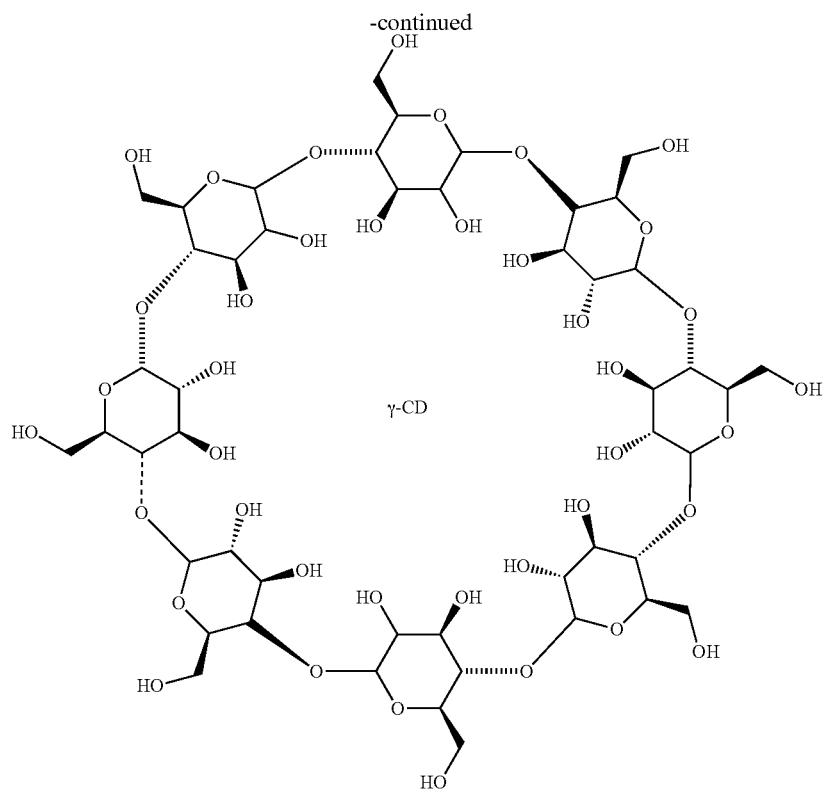
γ-CD

Cyclodextrin compounds according to the present invention include cyclodextrin per se, alkyl-cyclodextrin (R-CD) wherein "R" is methyl, ethyl, propyl or butyl; carboxyalkyl-cyclodextrin (CR-CD), etherified-cyclodextrin (RO-CD), hydroxyalkyl-cyclodextrin (HR-CD), glucosyl-cyclodextrin, di and triglycerides-cyclodextrin or a combination thereof and their pharmaceutically acceptable salts, which are water soluble in at least an amount of about 0.5 gr/100 ml at about 25° C.

The water-soluble cyclodextrin compound preferably used in the present invention refers to a cyclodextrin compound having water solubility of at least that of B-cyclodextrin (about 1.85 g/100 ml). Examples of such water-soluble cyclodextrin compound include hydroxypropylcyclodextrin, maltosylcyclodextrin and salts thereof. In particular, hydroxypropyl-β-cyclodextrin, maltosyl-β-cyclodextrin, and derivatives thereof are preferred.

Other preferred cyclodextrin compounds according to the present invention include methylcyclodextrins (products of the cyclodextrins methylation), such as 2-O-methyl β-cyclodextrin; dimethylcyclodextrin (DIMEB) (preferably substituted in 2 and in 6), trimethylcyclodextrin (preferably substituted in 2, 3 and 6), "random methylated" cyclodextrins (RAMEB or RM) (preferably substituted at random in 2, 3 and 6, but with a number of 1.7 to 1.9 methyl by unit glucopyrannose), hydroxypropylcyclodextrins (HPCD), hydroxypropylated cyclodextrins preferably substituted randomly mainly in position 2 and 3 (HP-βCD, HP-y CD), hydroxyethyl-cyclodextrins, carboxymethylethylcyclodextrins, ethylcyclodextrins, cyclodextrins amphiphilic obtained by grafting hydrocarbonated chains in the hydroxyl groups and being able to form nanoparticles, cholesterol cyclodextrins and triglycerides-cyclodextrins obtained by grafting cyclodextrins monoaminated (with a spacer arm) as described in Critical Review in Therapeutic drug Carrier Systems, Stephen D. Bruck Ed, Cyclodextrin-Enabling Excipient; their present and future use in Pharmaceuticals, D. Thomson, Volume 14, Issue 1 p 1-114 (1997), which is incorporated herein by reference in its entirety.

Most preferred cyclodextrins compounds in accordance with the present invention include I3-cyclodextrin with optionally a chemical function grafted on the glucopyrannose units, such as hydroxypropyl-βcyclodextrin (HPβCD), -βcyclodextrin (SBE(3CD), random methylated-βcyclodextrin (RMβCD), dimethyl-βcyclodextrin (DIMEβCD), trimethyl-βcyclodextrin (TRIMEβCD), hydroxybutyl-βcyclodextrin (HBβCD), glucosyl βcyclodextrin, maltosyl βcyclodextrin 2-0-methyl βcyclodextrin (Crysmeb) and their pharmaceutically acceptable salts, and any combination thereof.

The most preferred cyclodextrin in accordance with the present invention is hydroxypropyl-βcyclodextrin (also called HP-β-CD or HP-β-CD, hereinbefore or hereinafter).

The cyclodextrin compounds according to the present invention are produced by the well-known enzymatic degradation of starch, such as the method described in "Cyclodextrin Technology, J Szejtli, Kluwer Academic Publishers 1998, pp 1-78, which is incorporated herein by reference in its entirety, followed by grafting of an appropriate chemical group. They are commercially available from Roquette (France).

The most preferred pharmaceutical compositions comprise budesonide derivative and a cyclodextrin compound in a molar ratio between about 1-1 and about 1-100, preferably about 1:75, and most preferably about 1:50. The budesonide/hydroxypropyβ cyclodextrin concentration ratio is preferably in a molar ratio of about 1:50.

The pharmaceutical compositions according to the present invention comprising a cyclodextrin compound and a budesonide derivative may be prepared by adding an excess of budesonide derivative in powder form to an adequate amount of cyclodextrin in liquid solution. The liquid cyclodextrin solution is a water or water-alcohol or alcohol based solution such as ethanol. The budesonide derivative and the cyclodextrin compound are mixed under continuous agitation at room temperature. The excess amount of budesonide derivative is removed by filtration.

Both components are weighted to give a resulting budesonide derivative and cyclodextrine mixture in a weight concentration ratio of between about 1:1500 to about 1:2, preferably about 1:60 ratio.

The liquid mixture may then be dried during atomization by an appropriate well know technic of the art in order to produce a micronized dried powder. In such a case the pharmaceutical composition can also include a pharmaceutically acceptable excipient, such as a carrier as for example lactose, magnesium stearate, mannitol, polyols, leucine derivatives and the like.

The liquid mixture may also be added to a cyclodextrin in isotonic Buffer at the same concentration as the one of the cyclodextrin in liquid solution of the mixing step, to produce a pharmaceutical composition in liquid solution.

The pharmaceutical composition in liquid solution may also contain well known pharmaceutically acceptable excipients, such as isotonic buffers, preservatives, solvent or viscosity modulating agents and auxiliary substances. Appropriate isotonic buffer systems are based on sodium phosphate (PBS), sodium acetate or sodium borate.

Preservatives may be included to prevent microbial contamination of the pharmaceutical compositions during use. Suitable preservatives are, for example, benzalkonium chloride, chlorobutanol, methylparaben, propylparaben, phenylethyl alcohol, sorbic acid. Such preservatives are used typically in an amount of from about 0.01 to about 1% weight/volume.

Suitable auxiliary substances and pharmaceutically-acceptable salt are described in Remington's Pharmaceutical Sciences, 16th ed., 1980, Mack Publishing Co., edited by Oslo et al., which is incorporated herein in its entirety by reference.

Typically, an appropriate amount of a pharmaceutically-acceptable salt is used in a pharmaceutical composition of the present invention to render the composition isotonic. Examples of pharmaceutically acceptable substances include saline, Ringer's solution and dextrose solution. In accordance with the present invention, the pH of the solution is preferably from about 5 to about 8, and more preferably from about 7 to about 7.5.

The pharmaceutical compositions according to the present invention are useful for treatment and/or prevention of pulmonary inflammatory disease in a host mammal in need of such treatment, preferably for chronic obstructive pulmonary disease, such as chronic bronchitis, obstructive bronchiolitis, emphysema, pulmonary fibrosis, cystic fibrosis and most preferably for tobacco-induced chronic obstructive pulmonary disease and cystic fibrosis disease.

The pharmaceutical compositions of the present invention may be formulated into oral, parenteral or topical dosage forms, particularly in dosage forms for aerosol or nasal inhalation administration, a topical form of administration. The pharmaceutical compositions of the present invention may be delivered in solution, suspension, as micronized powder mixture and the like. Additionally, the pharmaceutical compositions of the present invention may be administered by, for example, a nebulizer, a metered dose inhaler or a dry powder inhaler or any other device that is designed for such topical administration.

The pharmaceutical compositions according to the present invention may be administered as a molecular dose in a range of from about 0.05 to about 1000 mcg, preferably from about 0.1 to about 500 mcg, and especially in the range of from about 50 to about 200 mcg per day.

A preferred pharmaceutical composition contemplated by the present invention comprises budesonide and cyclodextrin in liquid solution, most preferably budesonide and HP-β-cyclodextrin.

A most preferred pharmaceutical composition contemplated by the present invention contains budesonide and cyclodextrin in liquid solution at a concentration of about 100 μg/ml of budesonide in a solution of HP-β-cyclodextrin about 20 mM in an isotonic buffer.

The combination of a cyclodextrin compound with a budesonide derivative in the pharmaceutical compositions according to the present invention are preferably a complex budesonide derivate—cyclodextrin compound in a stoichiometric ratio of about 1:1 or about 2:1. Particularly, the complex budesonide with HP-β-cyclodextrin is in a stoichiometric ratio about 1:1.

The present invention further directed to the following:

(1) A pharmaceutical composition comprising a cyclodextrin compound and a budesonide derivative of formula I:

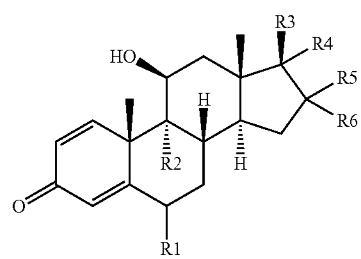

wherein R1 and R2 represent each independently hydrogen atom, halogen, $C_{1-5}$-alkyl, $C_{3-8}$-cycloalkyl, hydroxy, $C_{1-5}$-alkoxy, $C_{1-5}$-alkoxy-$C_{1-5}$-alkyl, $C_{1-5}$-alkyl optionally mono- or polysubstituted with a halogen atom, $C_{1-5}$-alkoxycarbonyl, $C_{1-5}$-alkoxycarbonyl-$C_{1-6}$-alkyl;

R3, R4, R5 and R6 represent each independently hydrogen, hydroxyl, $C_{1-5}$-alkoxy, $C_{1-5}$-alkoxycarbonyl, hydroxycarbonyl, $C_{1-5}$-alkylcarbonyl optionally mono- or polysubstituted with a halogen atom, $C_{1-5}$-alkylcarbonyloxy, $C_{3-8}$-cycloalkylcarbonyloxy, $C_{1-5}$ alkyl thio, $C_{1-5}$alkyl sulfonyl, $C_{1-5}$-alkylsulfinyl, furan, furan carbonyloxy, $C_{1-5}$-alkythiocarbonyl optionally mono- or polysubstituted with a halogen atom; and R4 and R5 optionally form together a hydrocarbon ring of 3 to 5 atoms, two carbon atoms optionally being replaced by an oxygen atom and the ring being optionally substituted by a $C_{1-5}$ alkyl group or a salt thereof with a pharmaceutically acceptable acid or base, or any optical isomer or mixture of optical isomers, including a racemic mixture or any tautomeric form thereof for use in the therapeutical and/or prevention treatment of pulmonary inflammatory disease in a host mammal in need of such treatment.

(2) The pharmaceutical composition according to claim 1, wherein the budesonide derivate/and the cyclodextrin compound are in a weight concentration ratio between about 1:1500 and about 1:2.

(3) The pharmaceutical composition according to claim 1, wherein the budesonide derivate/and the cyclodextrin compound are in a weight concentration ratio of about 1:60.

(4) The pharmaceutical composition according to claims 1-3, wherein the budesonide derivative is selected from the group consisting of mometasone furoate, fluticasone, fluticasone furoate, fluticasone propionate, betamethasone, betamethasone propionate, beclomethasone, budesonide or a combination thereof and their pharmaceutically acceptable salts or esters.

(5) The pharmaceutical composition according to any one of claims 1-4 comprising a budesonide derivative, wherein R1, R2, R6 are hydrogen; R3 is a hydroxyethanone group and R4 form with R5 a 1,3-dioxolan-2-yl)propyl or

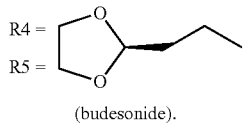

(budesonide).

(6) The pharmaceutical composition according to any one of claims 1-4 comprising a budesonide derivative, wherein R1 is hydrogen, R2 is Cl, R3 is furanecarboxyl, R4 is chloromethylcarbonyl and R5 and R6 are hydrogen (mometasone furoate).

(7) The pharmaceutical composition according to any one of claims 1-4 comprising a budesonide derivative, wherein R1 and R2 are Fluor, R3 is a fluoromethylthiocarbonyl, R4 is a furanecarboxyl and R5 and R6 are hydrogen (fluticasone furoate).

(8) The pharmaceutical composition according to any one of claims 1-4 comprising a budesonide derivative, wherein R1 and R2 are Fluor, R3 is a fluoromethylthiocarbonyl, R4 is a propylcarboxyl and R5 and R6 are hydrogen (fluticasone propionate).

(9) The pharmaceutical composition according to any one of claims 1-4 comprising a budesonide derivative wherein, R2 is chlorine, R1, R5 and R6 are hydrogen, R3 is propionyloxymethylcarbonyl and R4 is a propylcarbonyloxy group

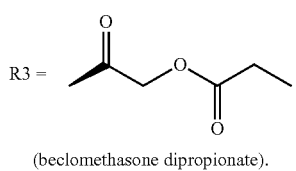

(beclomethasone dipropionate).

(10) The pharmaceutical composition according to any one of claims 1-9, wherein the budesonide derivative forms with the cyclodextrin compound a complex in an about 1:1 stoichiometric ratio.

(11) The composition according to anyone of claims 1-10, wherein the cyclodextrin compound has a water solubility of at least about 1.85 g/100 ml.

(12) The composition according to any one of claims 1-11, wherein the cyclodextrin compound is selected from the group consisting of: β-cyclodextrin, hydroxypropyl-βcyclodextrin, random methylated-βcyclodextrin, dimethyl-βcyclodextrin, trimethyl-βcyclodextrin, hydroxypropyl β-cyclodextrin, hydroxybutyl βcyclodextrin, glucosyl-β cyclodextrin, maltosyl-βcyclodextrin, 2-0-methyl-βcyclodextrin or a combinations thereof and their pharmaceutically acceptable salts.

(13) The composition according to any one of claims 1-12, wherein the cyclodextrin compound is hydroxypropyl β-cyclodextrin.

(14) The composition according to any one of claims 1-13, wherein the pulmonary inflammatory disease is a chronic obstructive disease.

(15) A method for prophylactic treatment of pulmonary inflammatory disease comprising an administration to a patient in need of such treatment of an effective dose of the composition according to any one of claims 1-14.

(16) A method for therapeutic treatment of pulmonary inflammatory disease comprising an administration to a patient in need of such treatment of an effective dose of the composition according to any one of claims 1-14.

(17) A method of treatment according to claim 15 or 16, wherein the cyclodextrin compound and the budesonide derivative are administered respectively at a nominal dosage of about 0.1 mg and about 25 mg/dose.

(18) An inhalation system for the treatment of pulmonary inflammatory disease in a patient of need thereof comprising the pharmaceutical composition according to claims 1-14.

(19) A pharmaceutical composition comprising about 250 μ/ml budesonide and about 20 mM HP-β-CD.

(20) A pharmaceutical composition comprising about 100 μ/ml budesonide and about 20 mM HP-β-CD.

(21) A pharmaceutical composition comprising about 250 μ/ml budesonide and about 10 mM HP-β-CD.

(22) A pharmaceutical composition comprising about 100 μ/ml budesonide and about 10 mM HP-β-CD.

(23) A pharmaceutical composition comprising about 100 μ/ml fluticasone and about 10 mM HP-β-CD.

(24) A pharmaceutical composition comprising about 40 μ/ml fluticasone and about 10 mM HP-β-CD.

(25) A pharmaceutical composition comprising about 40 μ/ml beclomethasone and about 10 mM HP-β-CD.

(26) A pharmaceutical composition of claims 19-25, wherein the pharmaceutical composition is a solution.

(27) A pharmaceutical composition of claim 26, wherein the solution has a pH of from about 5 to about 8.

(28) A pharmaceutical composition of claim 26, wherein the solution has a pH of from about 7 to about 7.5.

(29) A pharmaceutical composition of claim 26, wherein the pharmaceutical composition is a solution and the solution is spray-dried to generate a powder.

(30) A pharmaceutical composition of claim 29, wherein the powder comprises particles of about 3 microns.

(31) A pharmaceutical composition comprising a budesonide derivative and a cyclodextrin for delivering the budesonide derivative in a molecular dose in a range of from about 0.05 to about 1000 mcg.

(32) A pharmaceutical composition comprising a budesonide derivative and a cyclodextrin for delivering the budesonide derivative in a molecular dose in a range of from about 0.1 to about 500 mcg.

(33) A pharmaceutical composition comprising a budesonide derivative and a cyclodextrin for delivering the budesonide derivative in a molecular dose in a range of from about 50 to about 200 mcg per day.

(34) A pharmaceutical composition of claims 31-33, wherein the budenoside derivative is budenoside and the cyclodextrin compound is HP-β-CD.

(35) A pharmaceutical composition of claims 31-33, wherein the budenoside derivative is betamethasone and the cyclodextrin compound is HP-β-CD.

(36) A pharmaceutical composition of claims 31-33, wherein the budenoside derivative is fluticasone and the cyclodextrin compound is HP-β-CD.

(37) A pharmaceutical composition of claims 31-33, wherein the budenoside derivative is beclomethasone and the cyclodextrin compound is HP-β-CD.

(38) A pharmaceutical composition comprising a complex of a budesonide derivative and a cyclodextrin compound in a stoichiometric ratio of from about 1:1 to about 2:1.

(39) A pharmaceutical composition comprising a complex of a budesonide derivative and a cyclodextrin compound in a stoichiometric ratio of about 1:1.

(40) A pharmaceutical composition of claims 38-39, wherein the budenoside derivative is budenoside and the cyclodextrin compound is HP-β-CD.

(41) A pharmaceutical composition of claims 38-39, wherein the budenoside derivative is fluticasone and the cyclodextrin compound is HP-β-CD.

(42) A pharmaceutical composition of claims 38-39, wherein the budenoside derivative is beclomethasone and the cyclodextrin compound is HP-β-CD.

(43) A method of treating a pulmonary inflammatory disease in a host mammal in need of such treatment, the method comprising
administering to the host mammal a pharmaceutical composition of anyone of claims 1-14, 19-42 and 58.

(44) A method of reducing inflammatory cells in lung tissue in a host mammal in need of such treatment, said methods comprising
administering to the host mammal a pharmaceutical composition of anyone of claims 1-14, 19-42 and 58.

(45) A method of decreasing ozone-induced KC production in lung tissue in a host mammal in need of such treatment, said methods comprising
administering to the host mammal a pharmaceutical composition of anyone of claims 1-14, 19-42 and 58.

(46) A method of decreasing IL13 in lung tissue in a host mammal in need of such treatment after allergen exposure, said methods comprising
administering to the host mammal a pharmaceutical composition of anyone of claims 1-14, 19-42 and 58.

(47) A method of decreasing bronchial hyper-responsiveness in a host mammal in need of such treatment, said methods comprising
administering to the host mammal a pharmaceutical composition of anyone of claims 1-14, 19-42 and 58.

(48) A method of decreasing IL17 levels in a host mammal in need of such treatment, said methods comprising
administering to the host mammal a pharmaceutical composition of anyone of claims 1-14, 19-42 and 58.

(49) A method of decreasing CXCL-1 levels in a host mammal in need of such treatment, said methods comprising
administering to the host mammal a pharmaceutical composition of anyone of claims 1-14, 19-42 and 58.

(50) A method of decreasing neutrophils in lung tissue in a host mammal in need of such treatment after cigarette smoke exposure, said methods comprising
administering to the host mammal a pharmaceutical composition of anyone of claims 1-14, 19-42 and 58.

(51) A method for detecting and quantifying HP-β-CD in a composition containing an active ingredient and HP-β-CD without any separation or extraction step on the composition, wherein the HP-β-CD contains thereon a hydroxypropyl group, the method comprising:
using 1H NMR analysis of the hydroxypropyl group on the HP-β-CD to detect and quantify HP-β-CD in the composition.

(52) A method of claim 51 wherein the composition is a solution.

(53) A method of claim 51 or 52, wherein the active ingredient is a budenoside drivative.

(54) A method of claim 51 or 52, wherein the budenoside derivative is budesonide.

(55) A method of claim 51 or 52, wherein the budenoside derivative is fluticasone.

(56) A method of claim 51 or 52, wherein the budenoside derivative is beclomethasone.

(57) A method of claim 51 or 52, wherein the budenoside derivative is betamethasone.

(58) A pharmaceutical composition of claims 38-39, wherein the budenoside derivative is betamethasone and the cyclodextrin compound is HP-β-CD.

The following examples, references, and figures are provided to aid the understanding of the present invention. It is understood that modifications can be made in the procedures set forth without departing from the invention.

BRIEF DESCRIPTION OF THE DRAWINGS

The foregoing and other objects, advantages and features of the present invention, and the manner in which the same are accomplished, will become more readily apparent upon consideration of the following figures and examples, wherein.

Examples of various embodiments of the present invention will now be provided to illustrate the invention, but are not intended to be limiting thereof. Parts and percentages are by weight unless otherwise specified.

EXAMPLE 1

Pharmaceutical Composition of Budesonide with HPβ-Cyclodextrin in Solution

Budesonide is purchased from Indis (Belgium) and hydroxypropyl-beta-cyclodextrin, from Roquette (France). Commercial budesonide suspension at about 250 μg/ml (Pulmicort®) is purchased from AstraZeneca (Sweden).

Figure 1:
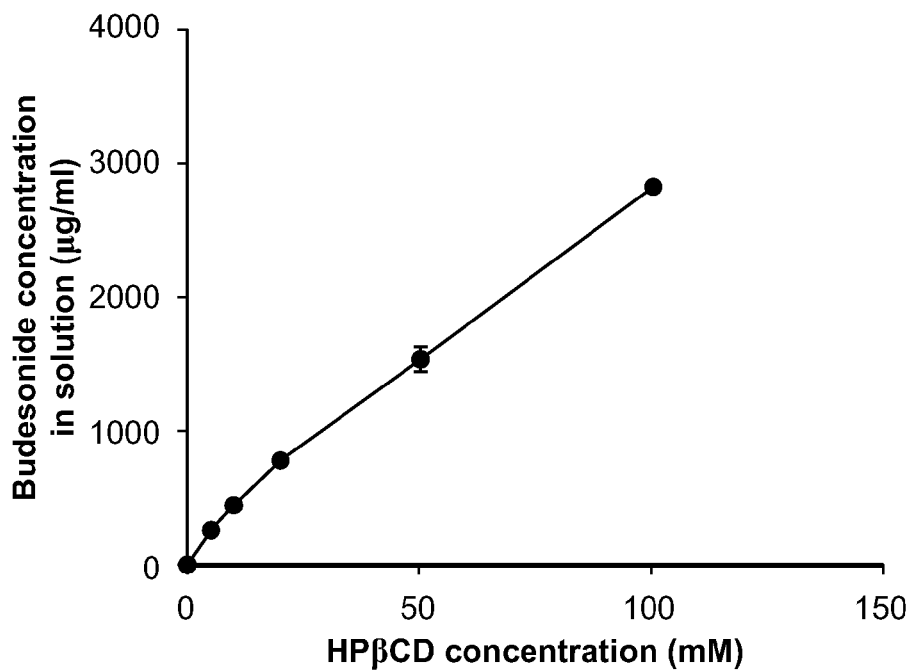
FIG. 1 is directed to a solubility diagram of budesonide in water solution with increasing concentration of HP-β-cyclodextrin (HPβCD)

In FIG. 1, the pharmaceutical composition in solution is prepared by adding excess budesonide in a powder form to a cyclodextrin solution of a precise concentration of about 5, about 10, about 25, about 50 and about 100 mM in water (the calculated and exactly weighed amount of cyclodextrin is corrected for water content by calculating the molarity using a Karl-Fischer titrator). The mixture process takes about 24 hours at room temperature under a continuous agitation of about 350 rpm. The excess amount of budesonide is removed by filtrating the resulting mixture with a 0.22 μm filter unit. The budesonide concentration in solution is verified with a validated HPLC method and the mixture is then diluted with a PBS-cyclodextrin solution (at the same precise concentration of about 5, about 10, about 25, about 50 and about 100 mM than before) to reach the required budesonide concentration for in-vivo testing.

At such concentrations, for example, about 100 μg/ml or about 250 μg/ml, budesonide is soluble in water/PBS and the pharmaceutical compositions appear as a clear and transparent inhalation solution.

EXAMPLE 1a: With about 100 μg/ml Budesonide and about 10 mM HP-β-CD

A preferred pharmaceutical formulation for inhalation solution comprises about 100 μg/ml of budesonide and about 10 mM of hydroxypropyl beta cyclodextrin. The solution is prepared by dissolving about 0.6979 g of HP-β-CD 5% water (corrected for its water content) in 50 ml of purified, pyrogen free water (or sterile PBS), adding excess budesonide and stir at room temperature for about 24 hours at about 350 rpm. The budesonide in excess is removed by filtration through a 0.22 μm filter unit and the resulting solution is dosed with a validated HPLC method. The resulting solution is then diluted with an HP-β-CD solution (in PBS or water) at about 10 mM to reach the concentration of about 100 μg/ml of budesonide. The isotonicity is reached by adding NaCl. Preferably, the final solution is sterilized by filtration through a 0.22 μm polypropylene membrane or by a steam sterilization process.

EXAMPLE 1b: With about 100 μg/ml Budesonide and about 20 mM HP-β-CD

A second preferred pharmaceutical formulation for inhalation solution comprises about 100 μg/ml of budesonide and about 20 mM of hydroxypropyl beta cyclodextrin. The solution is prepared by dissolving about 1.3958 g of HP-β-CD about 5% water (corrected for its water content) in about 50 ml of purified, pyrogen free water (or sterile PBS), adding excess budesonide and stir for about 24 hours at about 350 rpm. The budesonide in excess is removed by filtration through a 0.22 μm filter unit and the resulting solution is dosed with a validated HPLC method. The resulting solution is then diluted with an HP-β-CD solution (in PBS or water) at about 20 mM to reach the concentration of about 100 μg/ml of budesonide. The isotonicity is reached by adding NaCl. Preferably, the final solution is sterilized by filtration through a 0.22 μm polypropylene membrane or by a steam sterilization process.

EXAMPLE 1c: With about 250 μg/ml Budesonide and about 20 mM HP-β-CD

A third preferred pharmaceutical formulation for inhalation solution comprises about 250 μg/ml of budesonide and about 20 mM of hydroxypropyl beta cyclodextrin. The solution is prepared by dissolving about 1.3958 g of HP-β-CD about 5% water (corrected for its water content) in about 50 ml of purified, pyrogen free water (or sterile PBS), adding excess budesonide and stir for about 24 hours at about 350 rpm. The budesonide in excess is removed by filtration through a 0.22 μm filter unit and the resulting solution is dosed with a validated HPLC method. The resulting solution is then diluted with an HP-β-CD solution (in PBS or water) at about 20 mM to reach the concentration of about 250 μg/ml of budesonide. The isotonicity is reached by adding NaCl. Preferably the final solution is sterilized by filtration through a 0.22 μm polypropylene membrane or by a steam sterilization process.

EXAMPLE 1d: With about 100 μg/ml Fluticasone and about 10 mM HP-β-CD

A fourth preferred pharmaceutical formulation for inhalation solution comprises about 100 μg/ml of Fluticasone and about 10 mM of hydroxypropyl beta cyclodextrin. The solution is prepared by dissolving about 0.6979 g of HP-β-CD about 5% water (corrected for its water content) in about 50 ml of purified, pyrogen free water (or sterile PBS), adding excess fluticasone and stir at room temperature for about 24 hours at about 350 rpm. The fluticasone in excess is removed by filtration through a 0.22 μm filter unit and the resulting solution is dosed with a validated HPLC method. The resulting solution is then diluted with an HP-β-CD solution (in PBS or water) at about 10 mM to reach the concentration of about 100 μg/ml of fluticasone. The isotonicity is reached by adding NaCl. Preferably, the final solution is sterilized by filtration through a 0.22 μm polypropylene membrane or by a steam sterilization process.

EXAMPLE 1e: With about 40 µg/ml Fluticasone and about 10 mM HP-β-CD

A fifth preferred pharmaceutical formulation for inhalation solution comprises about 40 µg/ml of Fluticasone and about 10 mM of hydroxypropyl beta cyclodextrin. The solution is prepared by dissolving about 0.6979 g of HP-β-CD about 5% water (t corrected for its water contain) in about 50 ml of purified, pyrogen free water (or sterile PBS), adding excess fluticasone and stir at room temperature for about 24 hours at about 350 rpm. The fluticasone in excess is removed by filtration through a 0.22 µm filter unit and the resulting solution is dosed with a validated HPLC method. The resulting solution is then diluted with an HP-β-CD solution (in PBS or water) at 10 mM to reach the concentration of about 40 µg/ml of fluticasone. The isotonicity is reached by adding NaCl. Preferably the final solution is sterilized by filtration through a 0.22 µm polypropylene membrane or by a steam sterilization process.

EXAMPLE 1f: With 40 µg/ml Belcomethasone and about 10 mM HP-β-CD

A seventh preferred pharmaceutical formulation for inhalation solution comprises about 40 µg/ml of Beclomethasone and about 10 mM of hydroxypropyl beta cyclodextrin. The solution is prepared by dissolving about 0.6979 g of HP-β-CD about 5% (corrected for its water content) in about 50 ml of purified, pyrogen free water (or sterile PBS), adding excess beclomethasone and stir at room temperature for about 24 hours at about 350 rpm. The beclomethasone in excess is removed by filtration through a 0.22 µm filter unit and the resulting solution is dosed with a validated HPLC method. The resulting solution is then diluted with an HP-β-CD solution (in PBS or water) at about 10 mM to reach the concentration of about 40 µg/ml of beclomethasone. The isotonicity is reached by adding NaCl. Preferably, the final solution is sterilized by filtration through a 0.22 µm polypropylene membrane or by a steam sterilization process.

EXAMPLE 2

Pharmaceutical Composition of Fluticasone with HP-β-Cyclodextrin in Powder Form

A preferred pharmaceutical formulation for inhalation solution comprises about 40 µg/ml of Fluticasone from ECIC and about 10 mM of hydroxypropyl beta cyclodextrin. The solution is prepared by dissolving about 0.6979 g of HP-β-CD about 5% water (corrected for its water content) in about 50 ml of purified, pyrogen free water, adding excess fluticasone and stir for about 24 hours at about about 350 rpm. The fluticasone in excess is removed by filtration through a 0.22 lam filter unit and the resulting solution is dosed with a validated HPLC method. The resulting solution is then diluted with an HP-β-CD solution at about 10 mM to reach the concentration of about 40 µg/ml of fluticasone. The final solution is spray dried with a ProCept spray drier-chiller in optimised conditions to obtain a reasonable powder yield (about >90%) with particles of about 3 microns. The spray drying's technic is well known by the man skilled in the art.

EXAMPLE 3

Evaluation of Pharmaceutical Composition from Example 1 in a Model of Airway Obstruction and Inflammation 3a: Sensitisation, Allergen Exposure and Therapeutic Protocol.

Treatment
OVA inhalation
D0    D7    D14    D21    D25 D26
IP OVA    IP OVA                    BHR measurement
                                    Sacrifice Wherein IP means intraperitoneal injection and BHR means bronchial hyper-responsiveness.

In order to study modulation of airway inflammation, BALB/c mice of about 6 to about 8 weeks old are sensitized by intraperitoneal injection of about 10 µg ovalbumin (OVA) (Sigma Aldrich, Schnelldorf, Germany) emulsified in aluminum hydroxide (AlumInject; Perbio, Erembodegem, Belgium) on days 0 (DO) and 7 (D7). Mice are subsequently exposed to allergens by daily inhalation of an aerosol of OVA about 1%, for about 30 minutes, generated by ultrasonic nebulizer (Devilbiss 2000), from day 21 to day 25. Mice are subjected to about 50 µl intra-nasal instillations from day 18 to day 24 and are sacrificed on day 26, as previously reported by Cataldo et al.: Am. J. Pathol. 161 (2):491-498 (2002), which is incorporated herein in its entirety by reference. Placebo mice are intra-nasal injected with PBS.

Materials and Methods

Male mice C57B1/6, six to eight weeks old, are purchased from Charles River (Koln, Germany) and bred in our facility. All animal experiments procedures are approved by the ethical committee of the University of Liege. Food and water are supplied ad libitum.

Materials

Phosphate Buffered Saline (PBS) is purchased from Lonza (Verviers, Belgium), hydroxypropyl-beta-cyclodextrin (degree of substitution with hydroxypropyl group: 0.62) is purchased from Roquette (France), budesonide is purchased from Indis (Belgium) and commercial budesonide suspension at 250 µg/ml (Pulmicort®) is purchased from AstraZeneca (Sweden). Metacholine is from Sigma-Aldrich (Germany). For mouse administration, hydroxypropyl-beta-cyclodextrin about (20 mM) is mixed with budesonide (about 250 µg/ml) and budesonide suspension (about 250 µg/ml) according to Example 1a above. All other materials are of analytical grade. Sterile, apyrogenic and isotonic cyclodextrin derivative-corticosteroid solutions are prepared at various concentrations. Solutions are tested following the Bacterial Endotoxin Test guidelines of FDA 35 2012 using Limulus Amebocyte Lysate (LAL) for sterile water for inhalation (<about 0.5 USP Units of Endotoxin/ml).

Bronchoalveolar Lavage Fluid (BALF)

Immediately after assessment of airway responsiveness and about 24 hours after the last allergen exposure, mice are sacrificed and a Bronchoalveolar lavage is performed using 4× about 1 ml of PBS-EDTA about 0.05 mM (Calbiochem, Darmstadt, Germany) as previously described by Cataldo D D, Tournoy K G, Vermaelen K et al.: Am J Pathol. 161(2): 491-498 (2002), which is incorporated herein by reference in its entirety.

BALF supernatant is collected for protein assessment while cells are used for differential cell counts. Differential cell counts based on morphologic criteria are carried out on cytocentrifuged preparations after staining with haematoxylin-eosin (Diff-Quick, Dade, Belgium). Cells are recovered by gentle manual aspiration. After centrifugation of bronchoalveolar fluid (BALF) (about 1200 rpm for about 10 minutes, at about 4° C.), the supernatant is frozen at about −80° C. for protein assessment and the cell pellet is resuspended in about 1 ml PBS-EDTA about 0.05 mM. The differential cell counts are performed on cytocentrifuged preparations (Cytospin) after staining with Diff-Quick (Dade, Belgium).

Pulmonary Histology and Tissue Processing

After BAL, the thorax is opened and the left main bronchus is clamped. The left lung is excised and frozen immediately at about −80° C. for protein extraction. The right lung is infused with 4 ml paraformaldehyde about 4%, embedded in paraffin and used for histology. Sections of about 5 μm thickness are cut off from paraffin and are stained with haematoxylin-eosin. The extent of peribronchial inflammation is estimated by a score calculated by quantification of peribronchial inflammatory cells, as previously described by Cataldo D D, Tournoy K G, Vermaelen K et al.: Am J Pathol. 161(2):491-498 (2002). A value of 0 is adjudged when no inflammation is detectable, a value of 1 when there is occasionally inflammatory cells, a value of 2 when most bronchi are surrounded by a thin layer (about 1 to about 5 cells) of inflammatory cells and a value of 3 when most bronchi are surrounded by a thick layer (>about 5 cells) of inflammatory cells. Since 6-8 randomly selected tissue sections per mouse are scored, inflammation scores are expressed as a mean value and can be compared between groups.

As stated above, the left lung is excised and frozen immediately at about −80° C. and then disrupted in liquid $N_2$ by using a Mikro-Dismembrator (Braun Biotech International, Gmbh Melsungen, Germany) to form a homogenized powder. This crushed lung tissue is incubated overnight at about 4° C. in a solution containing about 2 M urea, about 1 M NaCl and about 50 mM Tris (pH about 7.5) and subsequently centrifuged for about 15 min at about 16 000×g for protein extraction.

IL13 levels are measured in non-pooled lung protein samples by ELISA (duoset kit, R&D Systems, Abingdon, United Kingdom) following manufacturer's instructions.

Bronchial Responsiveness Measurement

Mice are anesthetized by intraperitoneal injection (about 200 μl) of a mixture of ketamine (about 10 mg/ml, Merial, Brussels, Belgium) and xylazine (about 1 mg/ml, VMD, Arendonk, Belgium). A tracheotomy is performed by inserting a 20 gauge polyethylene catheter into the trachea and ligating it around the catheter to avoid leaks and disconnections. Mice are ventilated with a flexiVent® small animal ventilator (SCIREQ, Montreal, Canada) at a frequency of about 250 breaths per minute and a tidal volume of about 10 ml/kg. A positive end expiratory pressure is set at about 2 hPa. Measurement started after about 2 minutes of mechanical ventilation. A sinusoidal about 1-Hz oscillation is then applied to the tracheal tube and is allowed a calculation of dynamic resistance, elastance, and compliance of the airway by multiple linear regressions. A second manoeuvre consisting in an about 8-s forced oscillatory signal ranging frequencies between about 0.5 and about 19.6 Hz allows measurement of impedance to evaluate tissue damping, tissue elastance, and tissue hysteresivity. Following measurement of baseline lung function, mice are exposed to a saline aerosol (PBS) is followed by aerosols containing increasing doses (about 3, about 6, about 9, about 12 g/l) of metacholine (ICN Biomedicals, Asse Relegem, Belgium). Aerosols are generated by the mean of an ultrasonic nebuliser (SYST'AM, LS 2000, Dupont Medical, Rhode-Saint-Genèse, Belgium) and is delivered to the inspiratory line of the FlexiVent® using a bias flow of medical air following the manufacturer's instructions. Each aerosol is delivered for about 2 minutes and periods of measurement as described above are made at one-minute intervals following each aerosol. The mean airway resistance after metacholine exposure is the main parameter measured during the challenge.

Statistical Analysis

Results of pulmonary histology levels are expressed as mean +/− SEM and the comparison between the groups is performed using a one-way analysis of variance follow by a Tukey posttest. Tests are performed using GraphPad Prism 5. Significance level: Alpha=about 0.05 (95% confidence intervals).

Pharmacological Results

Figure 2:
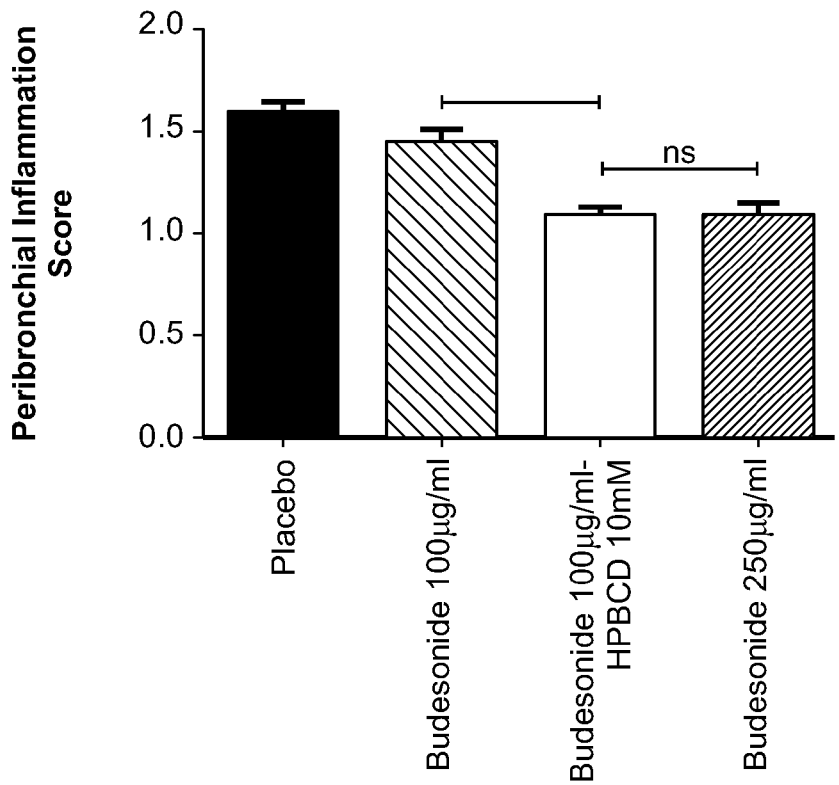
FIG. 2 is directed to a model of airway obstruction and inflammation: Peribronchial inflammation score measured in histology.

FIG. 2 illustrates Peribronchial inflammation score measured in histology with a placebo, budesonide about 100 μg/ml, a pharmaceutical composition according to Example la and budesonide about 250 μg/ml.

Ovalbumin exposed mice (Placebo) display a significant increase in inflammatory cells number in their lung tissues. Exposure to a complex of budesonide about 100 μg/ml and HP-β-CD about 10 mM induce display a significant decrease in inflammatory cells number when compared to placebo. The budesonide (about 100 μg/ml)-HP-β-CD (about 10 mM) complex induce the same inflammation decrease than budesonide alone at a higher concentration (about 250 μg/ml) and is significantly more effective than the budesonide alone at the same concentration about (100 μg/ml).

Figure 3:
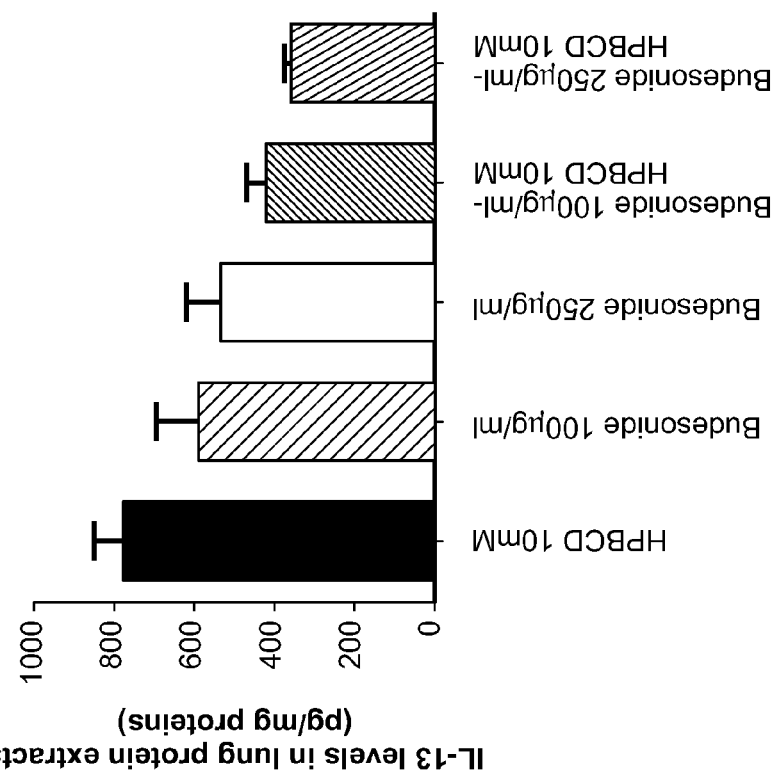
FIG. 3 is directed to IL13 levels measured in lung proteins extracts.

FIG. 3 illustrates: IL13 levels are measured in lung protein extracts.

The lungs are crushed using a Mikro-Dismembrator (Braun Biotech International, Gmbh Melsungen, Germany). Crushed lung tissue is incubated overnight at about 4° C. in a solution containing urea about 1M for protein extraction. The supernatant is stored at about −80° C. for ELISA tests.

Mouse display higher levels of IL13 in their lung tissue after allergen exposure when they are treated with budesonide about 250 μg/ml as compared to those that are treated with the complex budesonide about 250 μg/ml—cyclodextrin about 10 mM. Mice treated with budesonide about 100 μg/ml display in a similar manner higher IL13 levels than mice that are treated with budesonide about 100 μg/ml—cyclodextrin about 10 mM.

EXAMPLE 4

Evaluation of Pharmaceutical Composition from Example 1a, Example 1b and Example 1c in COPD Models Two different mice models are used to mimic chronic obstructive pulmonary disease (COPD). In the first model, C57BL/6 mice are exposed to a high concentration of ozone (O3), which is a highly reactive oxidant air pollutant. Inhaled O3 in animal models is responsible of airway inflammation (by neutrophil cells) and hyper-responsiveness. The second model is using tobacco smoke as cigarette is known to be the main driver of COPD. Cigarette smoke exposure also leads to an airway inflammation mediated by neutrophil cells). Ozone and cigarette are potent inducers of oxidative stress and this stress can lead to chronic inflammation as observed in long term study.

4. A Ozone Model

Ozone Exposure and Therapeutic Protocol

A schematic description of an experience under ozone exposure are reported hereafter:

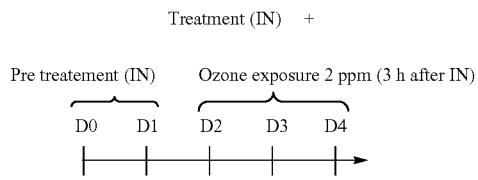

In the schematic description, C57BL/6 mice are firstly treated by an about 50l µl intra-nasal injection as a pre-treatment (between day 0 and day 1) before being exposed to a high concentration of ozone (about 2 ppm) during about 3 hours, preceded by a therapeutic about 50l µl intra-nasal injection about 3 hours before (between day 2 and day 4). Mice are sacrificed on day 5. Placebo mice are injected with PBS.

Bronchoalveolar lavage fluid (BALF) analysis, pulmonary histology analysis, bronchial responsiveness measurement and statistical analysis are the same as previously described in the Example 1 (airway inflammation and hyper-responsiveness). IL17 and KC (CXCL1) levels are measured in non-pooled lung protein samples by ELISA (duoset kit, R&D Systems, Abingdon, United Kingdom) following manufacturer's instructions.

Pharmacological Results

Figure 4:
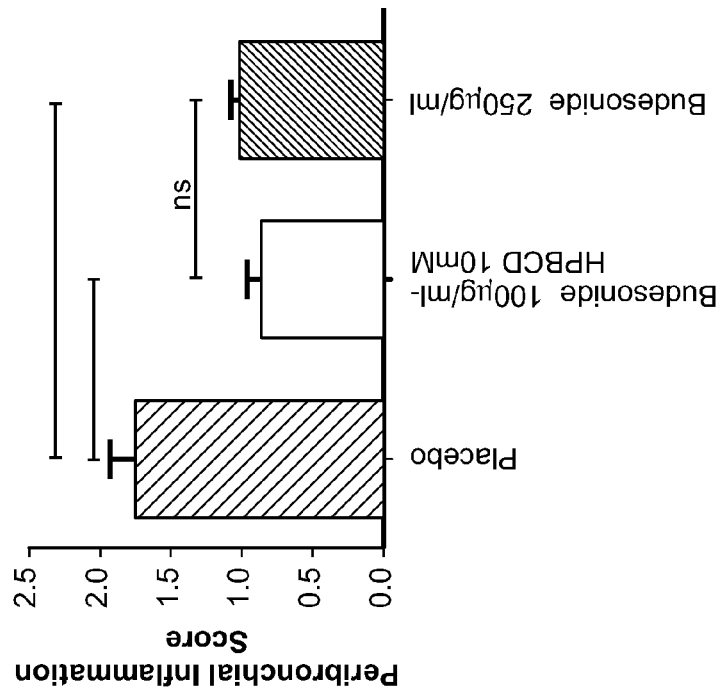
FIG. 4 is directed to a COPD model: peribronchial inflammation score measured in histology.

FIG. 4 illustrates Peribronchial inflammation score that is measured in histology for a placebo, a composition according to Example la and budesonide about 250 µg/ml.

Ozone-exposed mice (placebo) display a significant increase in inflammatory cells number in their lung tissues, as compared to other groups. Exposure to a complex comprising budesonide at about 100 µg/ml and HP-β-CD at 10 mM induce a significant decrease of inflammatory cells number when compared to placebo. The budesonide (about 100 µg/ml)-HP-β-CD (about 10 mM) complex induce the same inflammation decrease than budesonide alone at a higher concentration (about 250 µg/ml).

Figure 5:
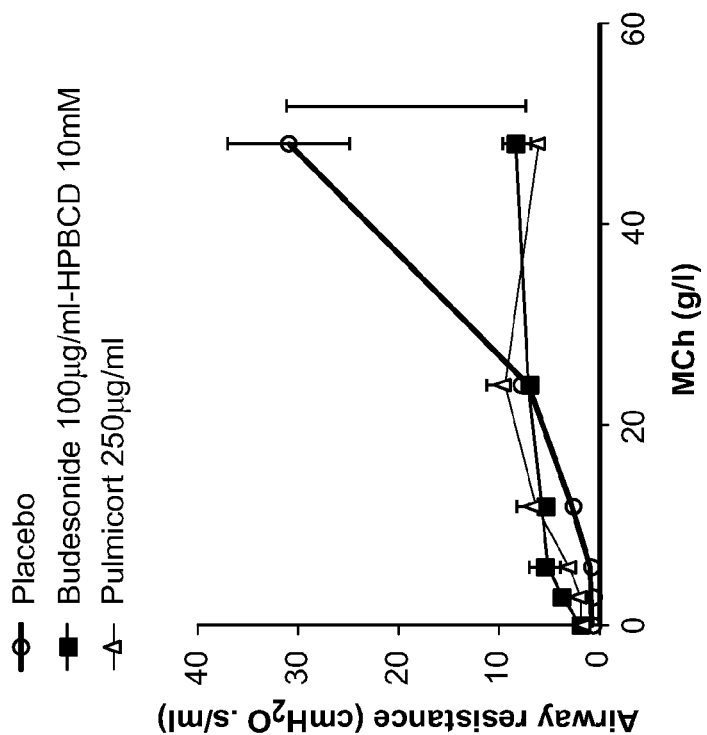
FIG. 5 is directed to airway responsiveness measurements: enhanced paused (Penh) was measured in mice after receiving placebo or treatments.

FIG. 5 illustrates Airway responsiveness measurement: Enhanced Paused (Penh) is measured in mice after receiving placebo or treatments with a pharmaceutical composition prepared according to Example la.

When compared to other groups, ozone exposure induces an expected significant increase of bronchial hyper-responsiveness in mice that are submitted to metacholine challenge. When compared to placebo group, a complex comprising budesonide at about 100 µg/ml and HP-β-CD at 10 mM induces a significant decrease of bronchial hyper-responsiveness at about 48 g/L of metacholine. The budesonide (about 100 µg/ml)-HP-β-CD (10 mM) complex induce the same bronchial hyper-responsiveness decrease than budesonide alone at a higher concentration (about 250 µg/ml).

Figure 6:
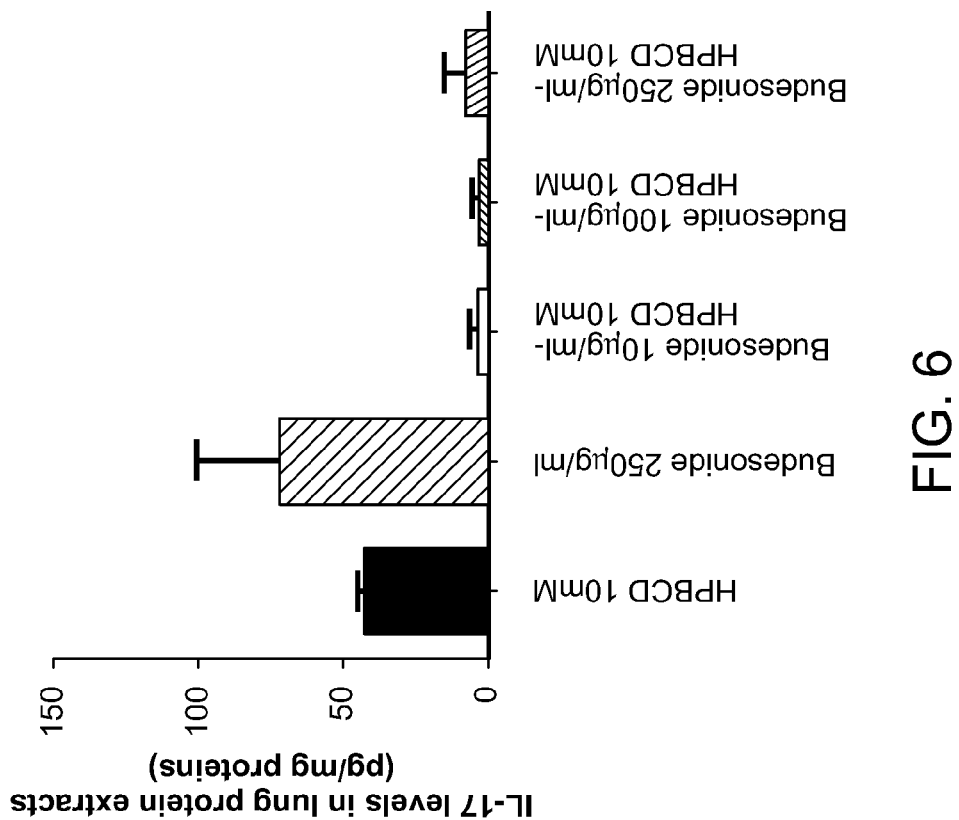
FIG. 6 is

FIG. 6 illustrates IL17 ELISA measurements in lung protein extracts of Ozone-exposed mice.

Different treatments with HP-β-CD and budesonide alone or in combination are compared. The pharmaceutical compositions are prepared according to Example la either in a combination mixture (budesonide-HP-β-CD) or with each active compound alone (budesonide about 250 µg/ml or HP-β-CD about 10 mM) in the same PBS buffer solution.

When compared to Budesonide-treated group (about 250 µg/ml), a complex comprising budesonide at about 250 µg/ml or about 100 µg/ml or about about 10 µg/ml and HP-β-CD at 10 mM induces a significant decrease in IL17 levels.

IL17 levels are increased after ozone exposure and might participate in the pathogenesis of ozone-induced neutrophils inflammation. This is the first demonstration that the budesonide-cyclodextrin complex given by inhalation is able to decrease ozone-induced IL17 levels.

Figure 7:
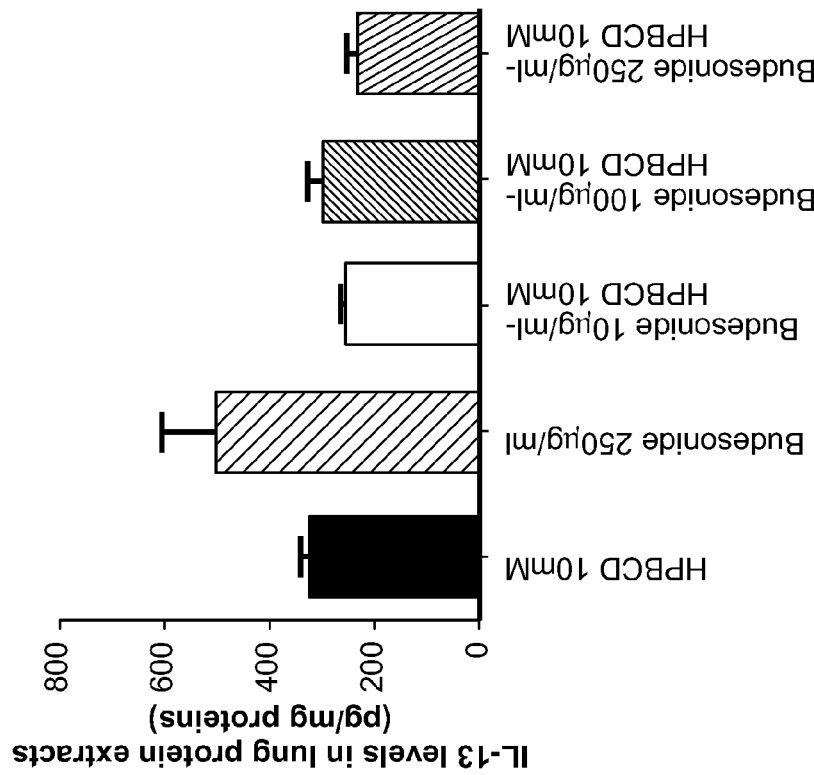
FIG. 7 is directed to IL13 ELISA measurements in lung protein extracts of ozone-exposed direct

FIG. 7 illustrates IL13 ELISA measurements in lung protein extracts of ozone-exposed mice.

Different treatments with HP-β-CD and budesonide alone or in combination are compared. The pharmaceutical compositions are prepared according to Example la either in a combination mixture (budesonide-HP-β-CD) or with each active compound alone (budesonide about 250 µg/ml or HP-β-CD about 10 mM) in the same PBS buffer solution.

When compared to Budesonide-treated group (about 250 µg/ml), a complex comprising budesonide at about 250 µg/ml or about 100 µg/ml or about 10 µg/ml and HP-β-CD at about 10 mM induces a decrease in IL17 levels.

IL13 has previously been shown to be modulated after ozone exposure and to participate in the airway dysfunction subsequent to ozone exposure. See, for example, Williams S., Nath P, Leung S, et al.: Eur Respir J. 32(3):571-8 (September 2008), which is incorporated herein by reference in its entirety. This is the first time that ozone-induced IL13 levels are shown to be significantly decreased by inhalation of a compound comprising budesonide. When compared to Budesonide-treated group (about 250 µg/ml), a complex comprising budesonide at about 250 µg/ml or about 100 µg/ml or about 10 µg/ml and HP-β-CD at about 10 mM induces a decrease in IL13 levels. Thus, the inhalation of budesonide-cyclodextrin complex decreases IL13 levels as compared to inhaled budesonide about 250 µg/ml.

Figure 8:
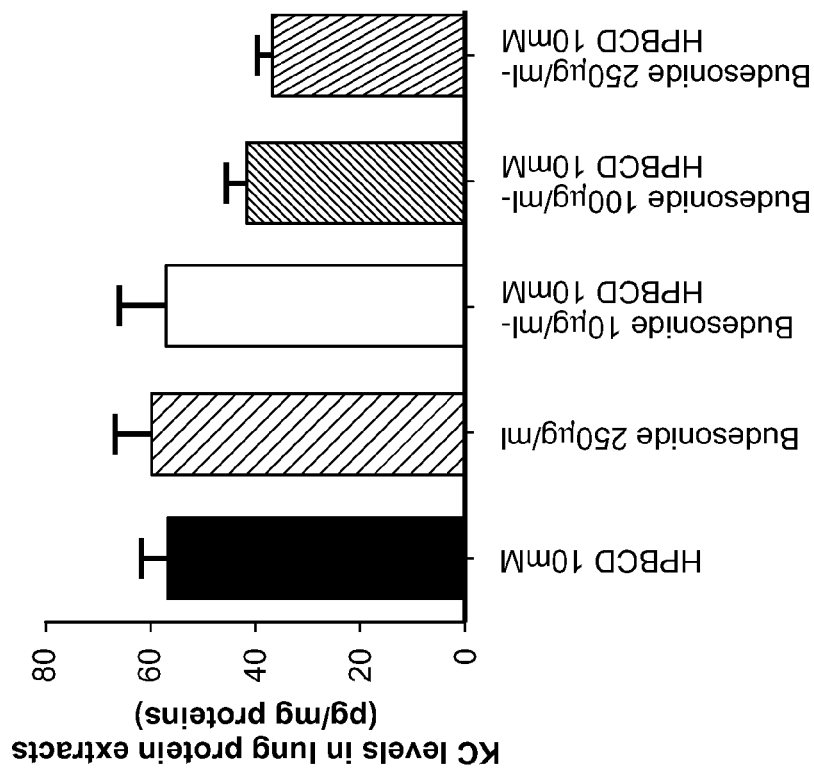
FIG. 8 is directed to KC (CXL1) ELISA measurements in lung protein extracts of ozone-exposed mice.

FIG. 8 illustrates KC (CXCL1) ELISA measurements in lung protein extracts of ozone-exposed mice.

Different inhalation treatments with HP-β-CD and budesonide alone or in combination are compared. The pharmaceutical compositions are prepared according to Example la either in a combination mixture (budesonide-HP-β-CD) or with each active compound alone (budesonide about 250 µg/ml or HP-β-CD about 10 mM) in the same PBS buffer solution.

When compared to Budesonide-treated group (about 250 µg/ml), a complex comprising budesonide at about 250 µg/ml or about 100 µg/ml and HP-β-CD at about 10 mM induces a decrease in KC levels.

This is the first demonstration that CXCL-1, a cytokine that plays a key role in the venue of neutrophils in bronchial walls following the exposure to irritants or oxidants, can be decreased by inhaled budesonide derivatives. This is only the budesonide-cyclodextrin complex that decreases ozone-induced KC production.

4.B Cigarette Smoke Exposure Model

Cigarette Exposure and Therapeutic Protocol

C57BL/6 mice are exposed to 10 cigarettes 5 days per week during 6 weeks using the Inexpose® system (Scireq, Montreal, Canada). Mice are treated by an about 50 µl intra-nasal injection 5 days per week during 6 weeks. Mice are sacrificed on day 43. Placebo mices also called sham exposed mices are injected with PBS.

Bronchoalveolar lavage fluid (BALF) analysis is the same as previously described in Example 3 (model of airway obstruction and inflammation).

Statistical Analysis

Results of inflammatory cells in bronchoalveolar lavage fluid number were expressed as mean +/− SEM and the comparison between the groups is performed using Mann-Whitney test. Tests are performed using GraphPad Prism 5. P values<0.05 are considered as significant. Pharmacological results In the present experiment, pharmaceutical composition according to Example 1b and 1c are used as specific inhalation solutions comprising:
about 100 µg/ml of budesonide and about 20 mM of hydroxypropyl beta cyclodextrin (Example 1b)
about 250 µg/ml of budesonide and about 20 mM of hydroxypropyl beta cyclodextrin (Example 1c)
in order to compare them to a solution of budesonide alone at about 500 µg/ml.

Figure 9:
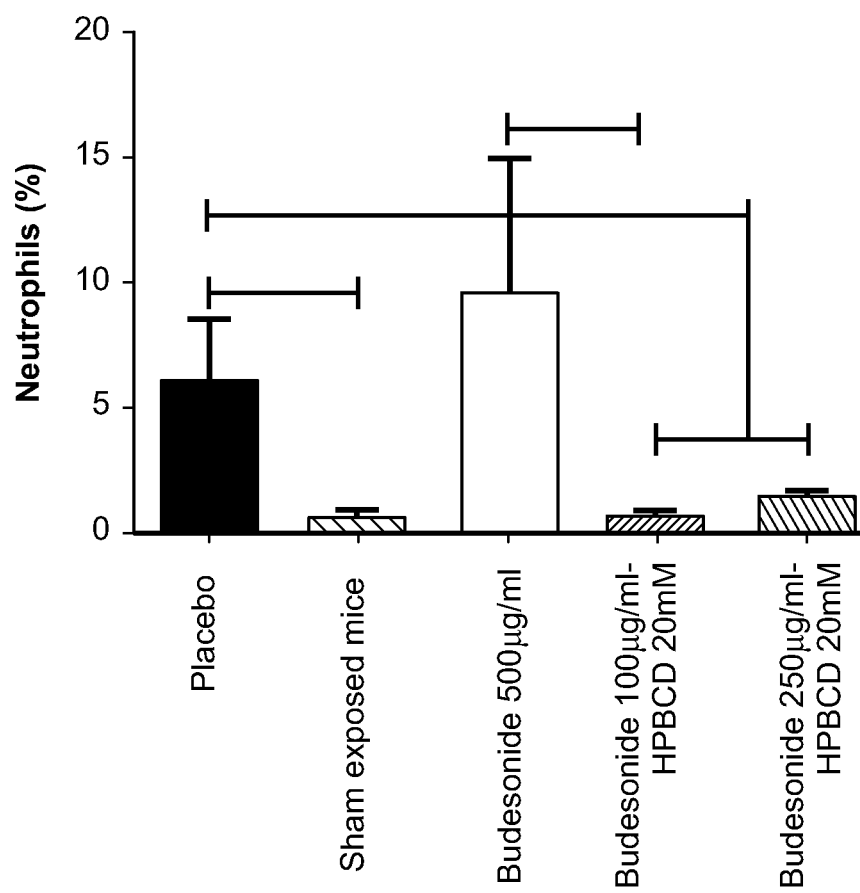
FIG. 9 is directed to the effects of budesonide-cyclodextrin on BALF neutrophil percentage.

FIG. 9 illustrates the effects of budesonide-cyclodextrin mixture on BALF neutrophil percentage.

standards at six concentration levels within the range of between about 0.05 mg/ml and about 5 mg/ml. At about 500 µl of these solutions, about 100 µl of D$_2$O buffer, about 100 µl of maleic acid (about 5 mM) and about 10 µl of TMSP are added for NMR analysis.

A preferred pharmaceutical composition budesonide-HP-β-CD is prepared according to Example 1a, with the exception that the isotonic buffer has been replaced by D$_2$O.

NMR Measurements

Budesonide HP-β-CD in D$_2$O is recorded at about 298 K on a Bruker Avance spectrometer operating at about 500.13 MHz for the proton signal acquisition. The instrument is equipped with a 5 mm TCI cryoprobe with a Z-gradient. A 1D NOESY-presat sequence (64 scans) is used in order to minimize the water signal. Maleic acid is used as internal standard for quantification and TMSP for the zero calibration.

In order to specifically detect HP-β-CD, the focus is on the hydroxypropyl group. Thus, the peak area of the doublet from the methyl group is measured at about 1.1 ppm, which is part of the hydroxypropyl group (FIG. 10B). This specific peak can also be quantified when the HP-β-CD is in presence of budesonide. The peak at about 1.1 ppm remains

TABLE 1

Percentage of neutrophils (+/−SEM) in BALF

|  | Sham-Exposed mice | Placebo (PBS) treated | Budesonide about 500 µg/ml | Budesonide about 100 µg/ml + CD about 20 mM | Budesonide about 250 µg/ml + CD about 20 mM |
|---|---|---|---|---|---|
| Neutrophils (%) | about 0.65 (+/−about 0.37) | about 6.08 (+/−about 2.51) | about 9.64 (+/−about 5.35) | about 0.62 (+/−about 0.27) | about 1.46 (+/−about 0.23) |

Cigarette smoke-exposed mice display a significant increase in neutrophil number in their bronchoalveolar lavage fluids (BALF), as compared to sham-exposed mice. Exposure to all tested concentrations of budesonide-HP-β-CD (about 20 mM) complexes induces a significant decrease in neutrophil number when compared to cigarette smoke-exposed mice. All the budesonide-HP-β-CD (about 20 mM) complexes induce a higher decrease than budesonide alone at a higher concentration (about 500 µg/ml). Budesonide alone is significantly not efficient enough to decrease the inflammation level in BALF of treated mice.

EXAMPLE 5

Complex Budesonide Derivative-Cyclodextrin

As HP-β-CD carbohydrates contain no chromophores, UV detection is not feasible. Until now, no techniques have been described for the quantification of HP-β-CD in a pharmaceutical aqueous solution. Since NMR spectroscopy is widely used to understand the interaction between CD and drugs and to evaluate the number of substituted glucopyranose units (molar substitution), 1H nuclear magnetic resonance spectrometry is applied for the detection and quantification of HP-β-CD in water.

Materials

HP-β-CD (molar substitution=0.64) is kindly donated by Roquette (France). Trimethylsilyl-3-propionic acid-d4 (TMSP) and deuterium oxide (about 99.96% D) are purchased from Eurisotop (Gif-sur-Yvette, France). Maleic acid is obtained from Sigma-Aldrich.

Samples Preparation

Figure 10A:
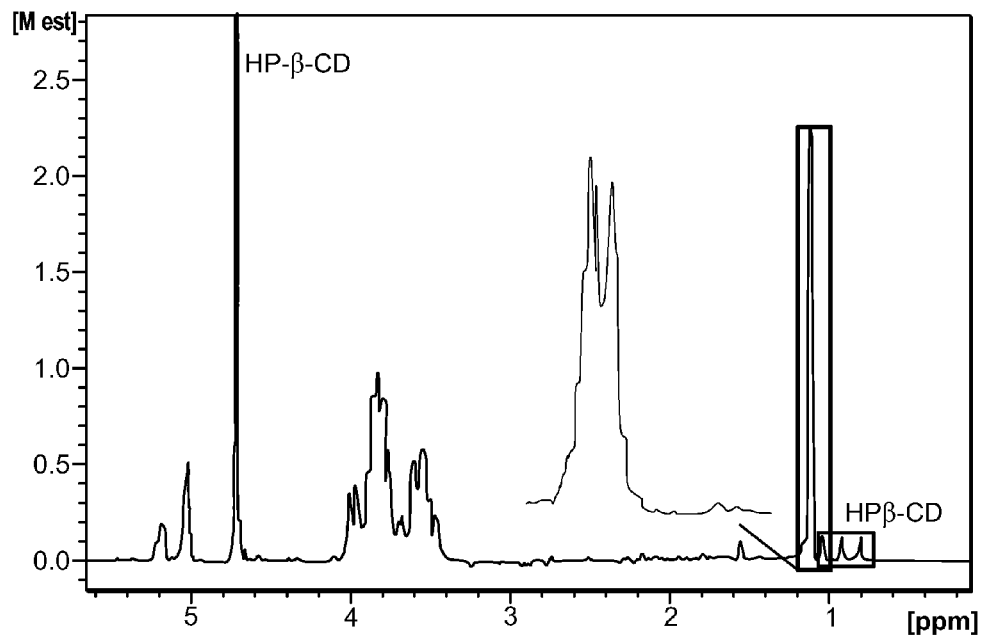
FIG. 10 is an illustration of an inclusion complex comprising a budesonide derivative and a cyclodextrin by $^1$H-NMR spectrum of a budesonide-Hydroxypropyl-β-cyclodextrin complex (FIG. 10a) compared to a reference $^1$H-RMN spectrum of Hydroxypropyl-β-cyclodextrin alone (FIG. 10b)
Figure 10B:
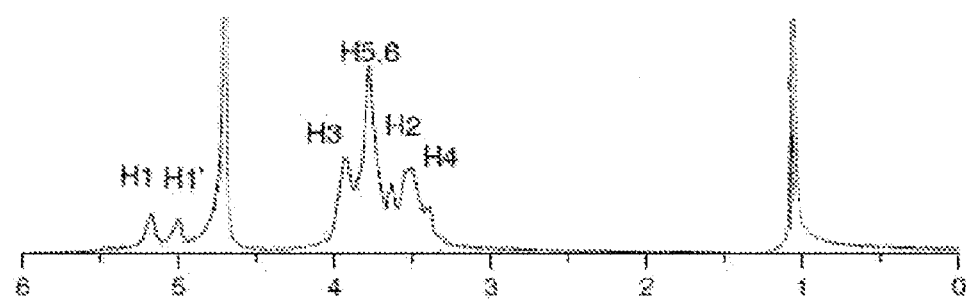

For the validation process, standard solutions of HP-β-CD are diluted in Milli-Q® water to obtain the calibration quantifiable and has kept the same area than without budesonide (FIG. 10A). Other peaks could also be used for the quantification of HP-β-CD including the peak at about 5.2 ppm.

Validation of the Method

The validation of the method is performed on three series of experiments. The following criteria are tested: selectivity, specificity (compared to (3-cyclodextrin), response function (calibration curve), linearity, precision (repeatability and intermediate precision), trueness, limit of detection (LOD), limit of quantification (LOQ), matrix effect and accuracy Total error is used as decision criterion for the validation process. The acceptance limits are set at about +/−7.5% and the minimum probability to obtain future results within these limits is set at 0=about 95% (β-expectation limits). The technique is therefore validated in the range described above.

Figure 11:
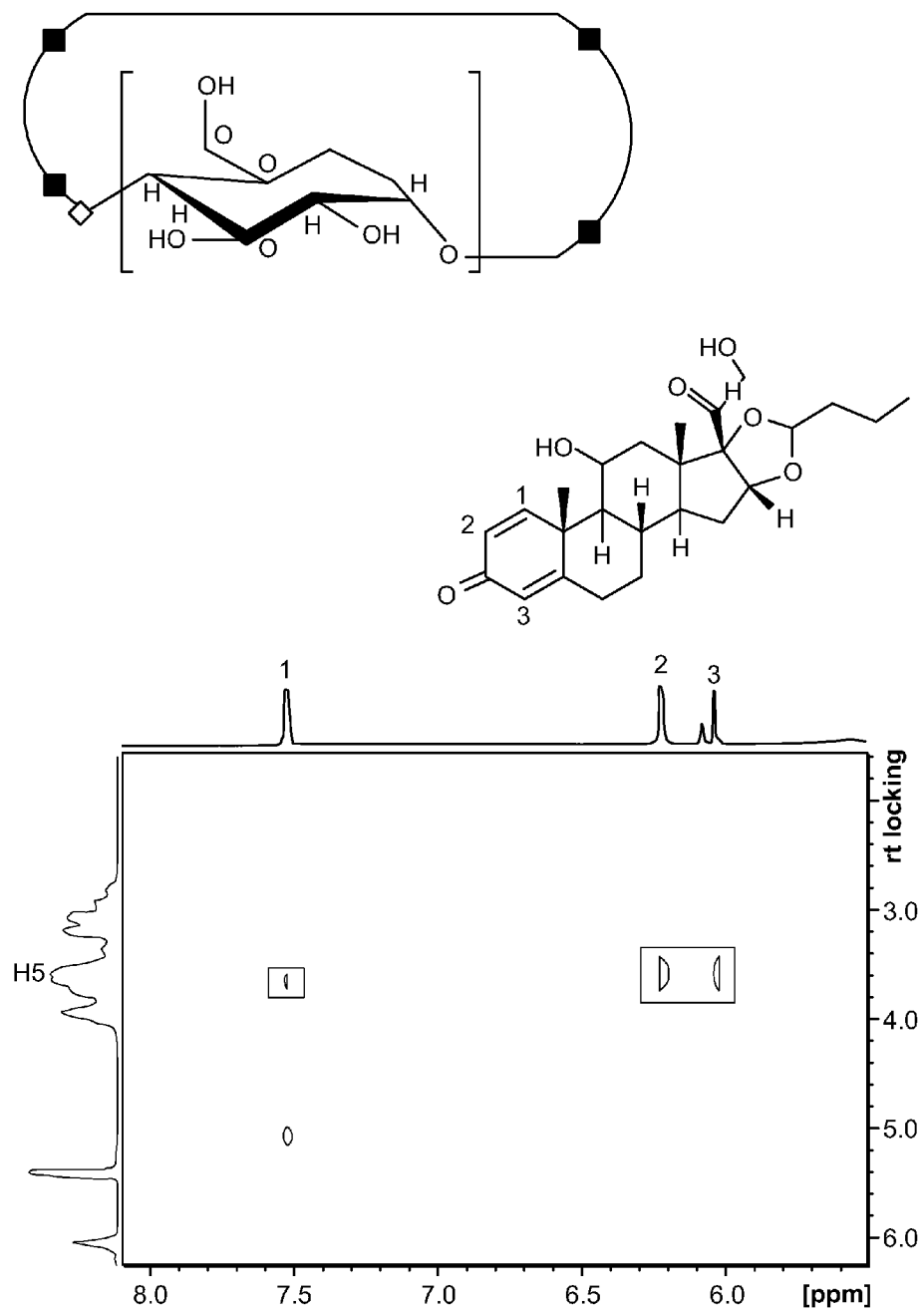
FIG. 11 is an illustration of an inclusion complex comprising a budesonide derivative and a cyclodextrin by 1D-COSY-NMR spectra of a budesonide-Hydroxypropyl-β-cyclodextrin complex.

FIG. 11 illustrates a 1D-COSY spectrum of the HP-β-CD-budesonide complex.

According to K. A. Connors: Chem. Rev. 97:1325-1357 (1997), which is incorporated herein by reference in its entirety, it is well known that H-3 and H-5 protons from HP-β-CD are located inside the cyclodextrin cavity, a correlation with theses protons suggest that budesonide or a part of budesonide is included inside HP-β-CD.

Indeed, two correlation spots (at about 7.4-7.5 ppm and about 5.8-6.1 ppm) indicate an interaction between budesonide aromatic rings H-5 HP-β-CD proton suggesting an inclusion leading to a water soluble complex.

EXAMPLE 6

Figure 12:
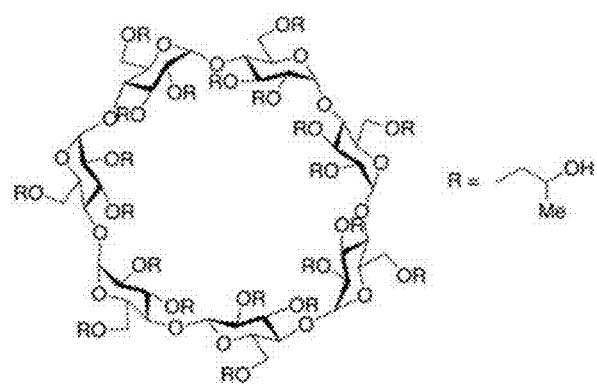
FIG. 12 is directed to the chemical structure of HP-β-CD.

Detection and Quantification of 2-Hydroxypropyl-β-Cyclodextrin in Solution by 1H NMR Spectroscopy as a Ttool for Quality Control Cyclodextrins (CDs) are cyclic oligosaccharides made up of linked a-1,4-glucopyranose units which form a truncated cone like structure comprising a hydrophobic cavity. The most used natural cyclodextrins are constituted of six, seven or eight glucopyranose units, commonly named a-, β- and γ-cyclodextrin, respectively. In order to reduce toxicity and to enhance water solubility, some derivatives are developed. Among them, 2-hydroxypropyl-β-cyclodextrin (HP-β-CD) (FIG. 12) is widely used in pharmaceutical formulations to enhance water solubility, stability and bioavailability of hydrophobic drugs by forming water soluble inclusion complexes.

According to USP and EP guidelines, characterization and quantification methods of pharmaceutical excipients should be defined. Given that HP-β-CD carbohydrates contain no chromophores, the UV detection is not feasible. Some techniques are therefore described for the quantification of CDs but none of them is developed for the quantification of HP-β-CD in a pharmaceutical aqueous solution. Since NMR spectroscopy is widely used to understand the interaction between CD and drugs and to evaluate the number of substituted glucopyranose units (molar substitution), 1H nuclear magnetic resonance spectrometry is applied in this study for the detection and quantification of HP-β-CD in water.

Experimental Methods

Materials

HP-β-CD (molar substitution=0.64) is kindly donated by Roquette (France). Trimethylsilyl-3-propionic acid-d4 (TMSP) and deuterium oxide (about 99.96% D) are purchased from Eurisotop (Gif-sur-Yvette, France). Maleic acid is obtained from Sigma-Aldrich. Statistical analyses are performed using the e-noval software (Arlenda, Liege, Belgium).

Sample Preparation

For the validation process, standard solutions of HP-β-CD were diluted in Milli-Q® water to obtain the calibration standards at six concentration levels within the range between about 0.05 mg/ml-about 5 mg/ml. At about 500 μl of these solutions, about 100 μl of D20 buffer, about 100 μl of maleic acid (about 5 mM) and about 10 μl of TMSP were added for NMR analysis.

NMR Measurements

All samples are recorded at about 298 K on a Bruker Avance spectrometer operating at about 500.13 MHz for the proton signal acquisition. The instrument is equipped with a 5 mm TCI cryoprobe with a Z-gradient. A 1D NOESY-presat sequence (64 scans) is used in order to minimize the water signal. Maleic acid is used as internal standard for quantification and TMSP for the zero calibration.

Results and Discussions

Detection and Quantification of HP-β-CD in water (1H-NMR)

Figure 13:
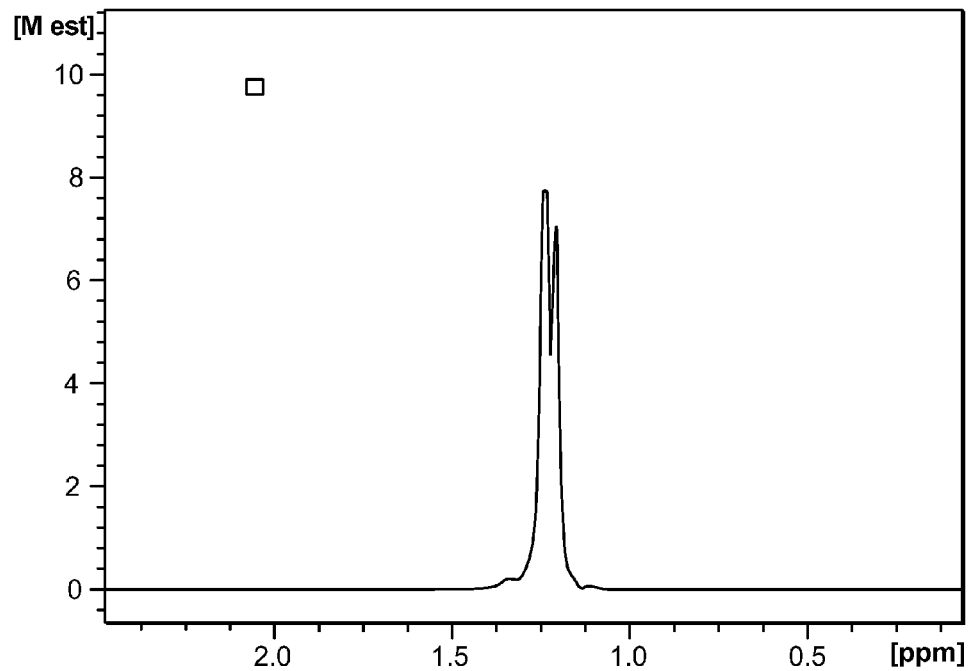
FIG. 13 is directed to 1H NMR spectra of HP-β-CD (δ 0.6-1.5) in water.

In order to specifically detect HP-β-CD, the focus is on the hydroxypropyl group. Thus, the peak area of the doublet from the methyl group at about 1.1 ppm is measured, which is part of the hydroxypropyl group (FIG. 13). This specific peak can also be quantified when the HP-β-CD is not alone in a water solution. Indeed, a solution comprising the HP-β-CD and a corticosteroid is realized, which is included into the cyclodextrin, and the peak at about 1.1 ppm was still quantifiable and has kept the same area than without the cortico steroid.

Validation of the Method

The validation of the method is performed on three series of experiments. The following criteria are tested: selectivity, specificity (compared to β-cyclodextrin), response function (calibration curve), linearity, precision (repeatability and intermediate precision), trueness, limit of detection (LOD), limit of quantification (LOQ), matrix effect and accuracy (FIG. 3). Total error is used as decision criterion for the validation process. The acceptance limits were set at about +/−7.5% and the minimum probability to obtain future results within these limits is set at β=about 95% (β-expectation limits).

Figure 14:
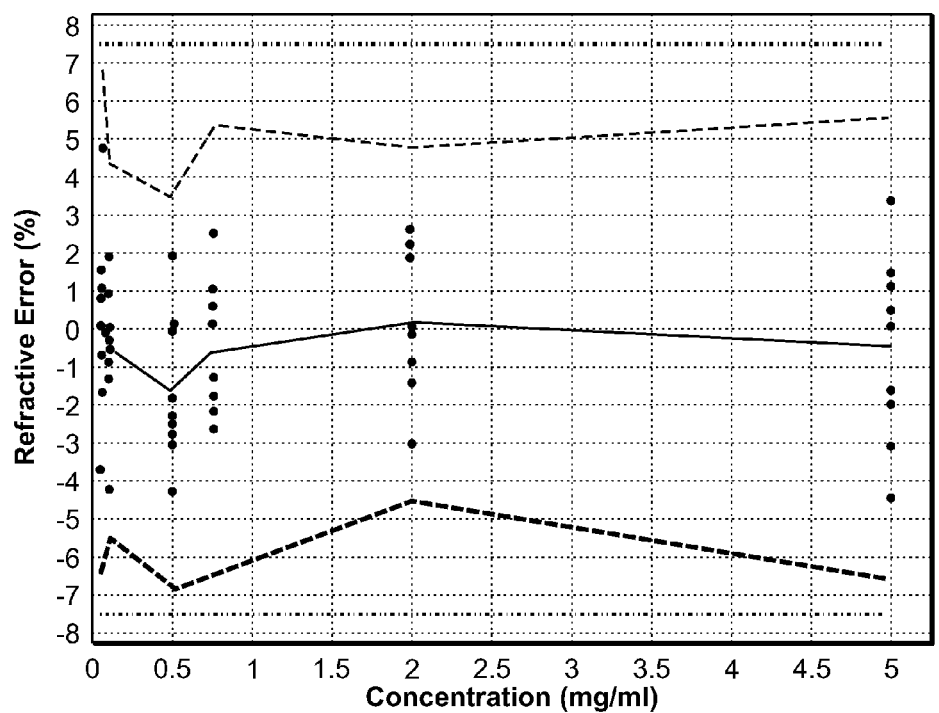
FIG. 14 is directed to an accuracy profile is obtained by considering Weighed (1/X) Quadratic Regression.

As shown in FIG. 14, the relative error of the back-calculated concentrations, represented by green dots, are spread around the relative bias (red line) and comprised in between the beta-expectation tolerance limits, represented by dashes lines. The technique is therefore validated in the range described above.

In this study, for the first time, a novel and useful analytical technique for the detection and the quantification of HP-β-CD in solution has been developed. This technique can be used for the dosage in pharmaceutical solutions such as parenteral solutions. This method displays at least two major advantages: rapidity and facility. Indeed, the NMR measurement only takes about 8 minutes, while the sample preparation only requires a simple addition of molecules in order to suppress the water signal and to quantify the peak area of hydroxypropyl. The measurements can therefore be realized directly into the pharmaceutical solution (containing the active ingredient) without any separation or extraction step.

EXAMPLE 7

Budesonide Effect on LPS/COPD Animal Model

Material and Methods

Mice

Male C57B1/6, 6 to 8 weeks old, are purchased from Charles River (Koln, Germany) and are bred in our facility. All animal experiment and procedures are approved by the ethical committee of the University of Liege. Food and water are supplied ad libitum.

Materials

Phosphate Buffered Saline (PBS) is purchased from Lonza (Verviers, Belgium), hydroxypropyl-beta-cyclodextrin is purchased from Roquette (France), budesonide is purchased from Indis (Belgium) and commercial budesonide suspension at about 250 μg/ml (Pulmicort®) is purchased from AstraZeneca (Sweden). For mouse administration, hydroxypropyl-beta-cyclodextrin (about 20 mM) is complexed with budesonide (about 250 μg/ml) and budesonide suspension (about 250 μg/ml) as the commercial formulation.

Lipopolysaccharide (LPS) Exposure Assay and Cyclodextrine-Budesonide Treatment

Mice (n=7/group) are anesthetized before daily instillations with about 2.5% isoflurane/oxygen mixture. Mice are instilled with about 50 μl of Phosphate Buffered Saline (PBS) (placebo group) or about 50 μl of hydroxypropyl-beta-cyclodextrin-budesonide complex or about 50 μl of a commercial budesonide suspension at about 250 μg/ml (Pulmicort®) at days 0, 1, 2, 3. Mice are sacrificed at day 4. Six hours after treatment administration, mice are intratracheally instilled with LPS (about 1 µg/100 µl PBS, Ultrapure lipopolysaccharide from *E. Coli*, InvivoGen, San Diego, Calif., USA), 2 times at days 1 and 3.

Pulmonary Cytology and Histology

At the end of the experimental protocol, animals are sacrificed and bronchoalveolar lavage fluid (BALF) is performed via intratracheal instillation of 4×1 ml PBS-EDTA solution, about 0.05 mM, (Calbiochem, Darmstadt, Germany). BALF supernatant is collected for protein assessment while cells are used for differential cell counts. Differential cell counts based on morphologic criteria are carried out on cytocentrifuged preparations after staining with haematoxylin-eosin (Diff-Quick, Dade, Belgium).

After BALF, left main bronchus is clamped and left lung is excised and preserved at about 80° C. The right lung is infused at a pressure of about 25 cm with about 4% paraformaldehyde and embedded in paraffin. Six sections of about 5 µm are randomly collected, are sectioned and are stained with hematoxylin and eosin (H.E). Each subsequent section is spaced about 50 µm from the previous one. Slides are scanned using a Hamamatsu nanozoomer HT 2.0 and inflammation is quantified on digitalized slides by applying a previously described inflammation scoring system. See, e.g., Cataldo et al.: Am J Pathol (2002), which is incorporated herein by reference in its entirety.

Results

Broncho-Alveolar Lavage Cytology

Figure 15:
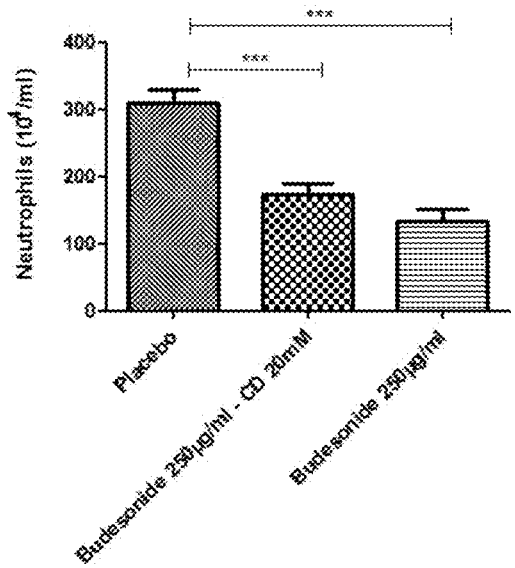
FIG. 15 is a measurements of neutrophil counts in BALF from LPS-exposed animals that are treated with placebo, budesonide suspension and hydroxypropyl-beta-cyclodextrin-budesonide complex.

The numbers of neutrophils measured in the BALF from experimental animals are significantly lowered after treatment with budesonide suspension and hydroxypropyl-beta-cyclodextrin-budesonide complex, as compared to the placebo-treated animals. See FIG. 15.

Measurements of Inflammation in Lung Parenchyma

Figure 16:
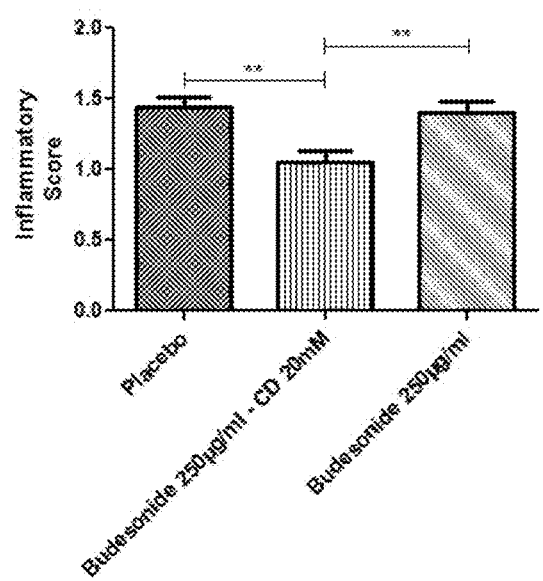
FIG. 16 is a measurement of inflammation score in LPS-exposed mice.

Surprisingly, animals exposed to LPS and treated with hydroxypropyl-beta-cyclodextrin-budesonide complex display a significant lowering of LPS-induced inflammation as compared with placebo and budesonide suspension-treated animals. See FIG. 16.

EXAMPLE 8

Betamethasone Dipropionate (Starting Material Micronized)

Solutions are prepared in an about 20 mM Crysmeb solution in PBS buffer. About 5.08 g Crysmeb are dissolved in Phosphate Buffered Saline (PBS) buffer. PBS is purchased from Lonza (Verviers, Belgium).

Add between about 25 and about 30 mg Betamethasone Dipropionate (in excess), to saturate the solution, and mix gently for about 48 hours at about 25° C.

Filtrate the saturated solution through 0.22 microns and assay the Betamethasone Dipropionate content in filtrate by the validated HPLC method.

The concentration of the Betamethasone Dipropionate solution prepared is about 147 g/ml.

EXAMPLE 8a: 100 µg/ml Betamethasone Dipropionate Solution

Dilute about 34 ml of the 147 µg/ml solution, as prepared above, to about 50 ml with about 20 mM Crysmeb PBS solution (HPLC Assay=about 99.00 µg/ml).

Sterilize the diluted solution by passing the solution through a 0.22µ filtration under laminar flux. The concentration of the sterilized Betamethasone Dipropionate solution is about 100 µg/ml.

EXAMPLE 8b: 50 µg/ml Betamethasone Dipropionate Solution

Dilute about 17 ml of 147 µg/ml solution, as prepared above, to about 50 ml with about 20 mM Crysmeb PBS solution (HPLC Assay=about 49.64 µg/ml).

Sterilize the solution by passing the solution through a 0.22µ filtration under laminar flux. The concentration of the sterilized Betamethasone Dipropionate solution is about 50 µg/ml.

EXAMPLE 8c: Reference Suspension

No commercial Betamethasone Dipropionate solution exists; therefore, a reference Betamethasone Dipropionate solution is prepared according to the following recipe:

| | |
|---|---|
| Betamethasone Dipropionate | 10.0 mg |
| Tween 80 (Polysorbate 80) | 00.1 mg |
| PBS buffer q.s. ad | 100.0 ml |

Prepare the suspension under laminar flux.

Note: Betamethasone Dipropionate degrades under autoclave; therefore, preparation should be prepared before use.

EXAMPLE 9

Fluticasone Propionate (Starting Material Micronized)

Both HPβCD and Crysmeb are able to solubilize Fluticasone Propionate (FP) according to the following preparation method.

EXAMPLE 9a: Co-Evaporated Intermediate Product

Dissolve about 1.5 g HPβCD in 100 ml pure Ethanol. Thereafter dissolve about 25 mg Fluticasone Propionate into 50 mg pure ethanol. Once dissolved, combine the solutions and evaporate under vacuum until dry.

EXAMPLE 9b: 250 pg/ml Fluticasone Propionate Solution

Disperse the co-evaporate, as prepared above in Example 8a, into about 100 ml PBS buffer to make a suspension. The suspension is sterilized by autoclave to produce a FP solution having a concentration of about 250 µg/ml FP and about 10 mM HPβCD (HPLC assay FP, about 238 µg/ml).

EXAMPLE 9c: 100 µg/ml Fluticasone Propionate Solution

Dilute the 250 µg/ml solution, as prepared above in Example 8b, with about 10 mM HPβCD Solution (about 8.4 ml 238 µg/ml+ about 11.6 ml HPβCD in PBS). The suspension is sterilized by autoclave to produce a FP solution having a concentration of about 100 µg/ml FP and about 10 mM HPβCD.

EXAMPLE 9d: 50 µg/ml Fluticasone Propionate Solution

Dilute the 250 µg/ml solution, as prepared above in Example 8b, with about 10 mM HPβCD Solution (about 4.2 ml, about 238 µg/ml+ about 15.6 ml HPβCD in PBS). The suspension is sterilized by autoclave to produce a FP solution having a concentration of about 50 µg/ml FP and about 10 mM HPβCD.

Reference product for Example 9 is Flixotide suspension.

EXAMPLE 10

Betamethasone Dipropionate Effect on LPS/COPD Animal Model

Material and Methods
Mice

Male C57B1/6, 6 to 8 weeks old, are purchased from Charles River (Koln, Germany) and are bred in our facility. All animal experiments and procedures are approved by the ethical committee of the University of Liege. Food and water are supplied ad libitum.

Materials

Phosphate Buffered Saline (PBS) is purchased from Lonza (Verviers, Belgium), crysmeb is purchased from Roquette (France), Betamethasone dipropionate is purchased from ACIC (Canada) and between 80 is purchased from ICI through Sigma Aldrich. For mouse administration, products produced under Example 8 are tested.

Lipopolysaccharide (LPS) Exposure Assay and Cyclodextrine-Betamethasone Dipropionate Treatment Mice (n=10/group) are anesthetized before daily instillations with about 2.5% isoflurane/oxygen mixture. Mice are instilled with about 50 µl of Phosphate Buffered Saline (PBS) (placebo group) or about 50 µl of Crysmeb-Betamethasone dipropionate complex or about 50 µl of a betamethasone suspension, as prepared according to Example 8, at days 0, 1, 2, 3. Mice are sacrificed at day 4. Six hours after treatment administration, mice are intratracheally instilled with LPS (about 1 µg/100 µl PBS, Ultra-pure lipopolysaccharide from *E. Coli*, InvivoGen, San Diego, Calif., USA), 2 times at days 1 and 3.

Pulmonary Cytology and Histology

At the end of the experimental protocol, animals are sacrificed and bronchoalveolar lavage fluid (BALF) is performed via intratracheal instillation of 4×1 ml PBS-EDTA 0.05 mM solution (Calbiochem, Darmstadt, Germany). BALF supernatant is collected for protein assessment while cells are used for differential cell counts. Differential cell counts based on morphologic criteria are carried out on cytocentrifuged preparations after staining with haematoxylin-eosin (Diff-Quick, Dade, Belgium).

After BALF, left main bronchus is clamped and left lung is excised and preserved at 80° C. The right lung is infused at a pressure of about 25 cm with about 4% paraformaldehyde and embedded in paraffin. Six sections of about 5 µm are randomly collected, are sectioned and are stained with hematoxylin and eosin (H.E). Each subsequent section is spaced about 50 µm from the previous one. Slides are scanned using a Hamamatsu nanozoomer HT 2.0 and inflammation is quantified on digitalized slides by applying a previously described inflammation scoring system. See, e.g., Cataldo et al.: Am J Pathol (2002), which is incorporated herein by reference in its entirety.

Results
Broncho-Alveolar Lavage Cytology

Figure 18:
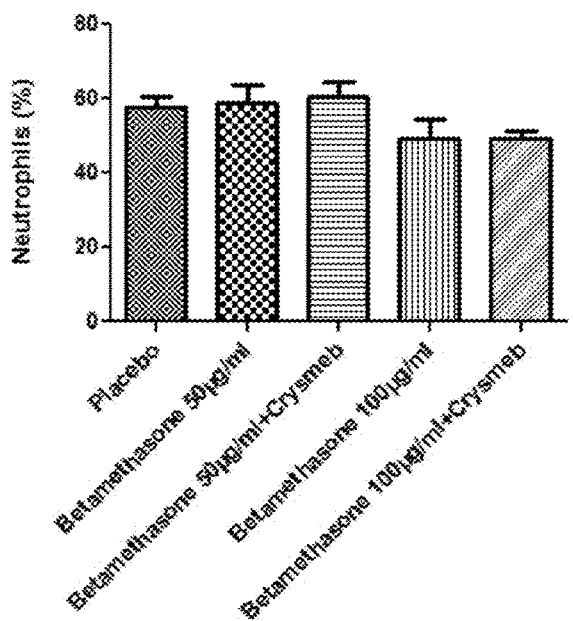
FIG. 18 is a measurements of neutrophil counts % in BALF from LPS-exposed animals that are treated with placebo, Crysmeb-betamethasone dipropionate complex and betamethasone 100 μg/ml suspension.
Figure 19:
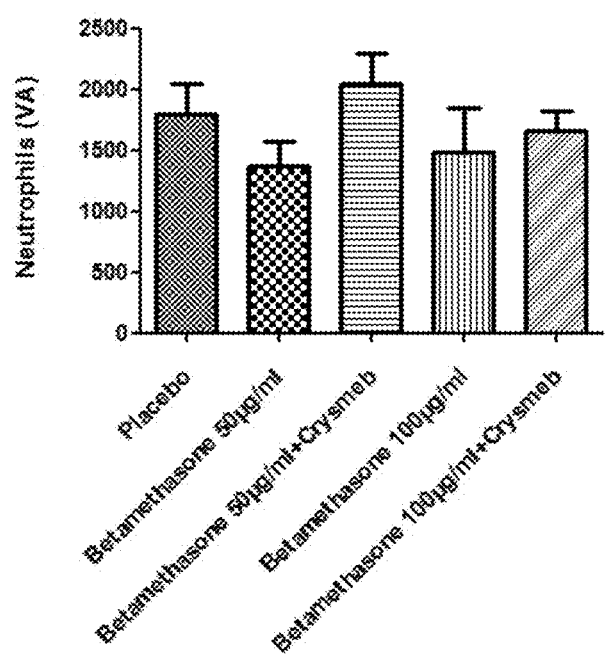
FIG. 19 is a measurements of neutrophil counts in BALF from LPS-exposed animals that are treated with placebo, Crysmeb-betamethasone dipropionate complex and betamethasone suspension.

The numbers of neutrophils measured in the BALF from experimental animals are lowered but not significantly after treatment by betamethasone dipropionate suspension and Crysmeb-betamethasone dipropionate complex, as compared to the placebo-treated animals. See FIG. 18 and FIG. 19.

Measurements of Inflammation in Lung Parenchyma

Figure 17:
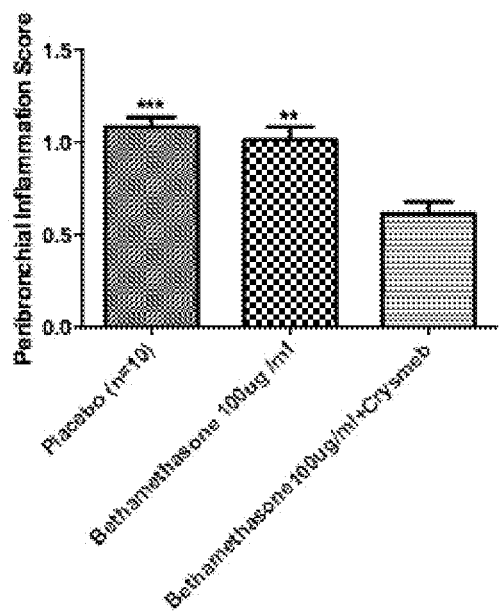
FIG. 17 is a measurement of inflammation score in LPS-exposed mice.

Surprisingly, animals that are exposed to LPS and treated with Crysmeb-betamethasone dipropionate complex, about 100 µg/ml, display a significant lowering of LPS-induced inflammation, as compared with placebo and betamethasone (about 100 µg/ml) suspension-treated animals. See FIG. 17.

Figure 20:
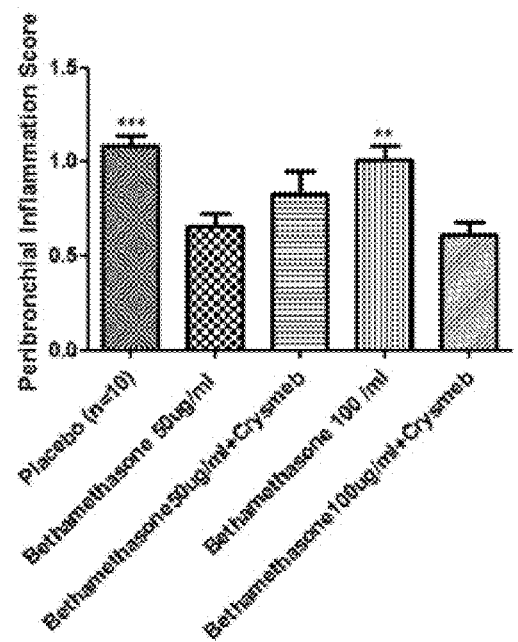
FIG. 20 is a measurement of inflammation score in LPS-exposed mice treated with placebo, Betamethasone dipropionate or Betamethasone dipropionate-Crysmeb complex at 2 concentrations.

And, animals that are exposed to LPS and treated with Crysmeb-betamethasone dipropionate complex about 50 and about 100 µg/ml and betamethasone about 50 µg/ml suspension display a significant lowering of LPS-induced inflammation, as compared with placebo-treated animals. Fluticasone reference about 100 µg/ml also displays a lowering effect vs placebo but not significant. Also Crysmeb-betamethasone dipropionate complex at about 100 µg/ml reduces significantly inflammation when compared to Fluticasone reference at about 100 µg/ml inflammation score. See FIG. 20.

EXAMPLE 11

Fluticasone Propionate Effect on LPS/COPD Animal Model

Material and Methods
Mice

Male C57B1/6, 6 to 8 weeks old are purchased from Charles River (Koln, Germany) and are bred in our facility. All animal experiments and procedures are approved by the ethical committee of the University of Liege. Food and water are supplied ad libitum.

Materials

Phosphate Buffered Saline (PBS) is purchased from Lonza (Verviers, Belgium), hydroxypropyl-beta-cyclodextrin is purchased from Roquette (France), Fluticasone propionate is purchased from ACIC (Canada) and commercial Fluticasone propionate suspension at about 250 µg/ml (Pulmicort®) is purchased from Glaxo SmithKline (UK). For mouse administration, hydroxypropyl-beta-cyclodextrin (about 10 mM) is complexed with Fluticasone propionate (about 250 µg/ml) according to Example 9 and Fluticasone propionate suspension (about 250 µg/ml) as the commercial formulation.

Lipopolysaccharide (LPS) Exposure Assay and Cyclodextrine-Fluticasone Propionate Treatment Mice (n=10/group) are anesthetized before daily instillations with about 2.5% isoflurane/oxygen mixture. Mice are instilled with about 50 µl of Phosphate Buffered Saline (PBS) (placebo group) or about 50 µl of hydroxypropyl-beta-cyclodextrin-Fluticasone propionate complex or about 50 µl of a commercial Fluticasone propionate suspension at about 250 µg/ml (Flixotide®) at days 0, 1, 2, 3. Mice are sacrificed at day 4. Six hours after treatment administration, mice are intratracheally instilled with LPS (about 1 µg/100 µl PBS, Ultra-pure lipopolysaccharide from *E. Coli*, InvivoGen, San Diego, Calif., USA), 2 times at days 1 and 3.

Pulmonary Cytology and Histology

At the end of the experimental protocol, animals are sacrificed and bronchoalveolar lavage fluid (BALF) is performed via intratracheal instillation of 4×1 ml PBS-EDTA 0.05 mM solution (Calbiochem, Darmstadt, Germany). BALF supernatant is collected for protein assessment while cells are used for differential cell counts. Differential cell counts based on morphologic criteria are carried out on cytocentrifuged preparations after staining with haematoxylin-eosin (Diff-Quick, Dade, Belgium).

After BALF, left main bronchus is clamped and left lung is excised and preserved at 80° C. The right lung is infused at a pressure of about 25 cm with about 4% paraformaldehyde and embedded in paraffin. Six sections of about 5 μm are randomly collected, are sectioned and are stained with hematoxylin and eosin (H.E). Each subsequent section is spaced about 50 μm from the previous one. Slides are scanned using a Hamamatsu nanozoomer HT 2.0 and inflammation is quantified on digitalized slides by applying a previously described inflammation scoring system. See, e.g., Cataldo et al.: Am J Pathol (2002), which is incorporated herein by reference in its entirety.

Results
Broncho-Alveolar Lavage Cytology

Figure 21:
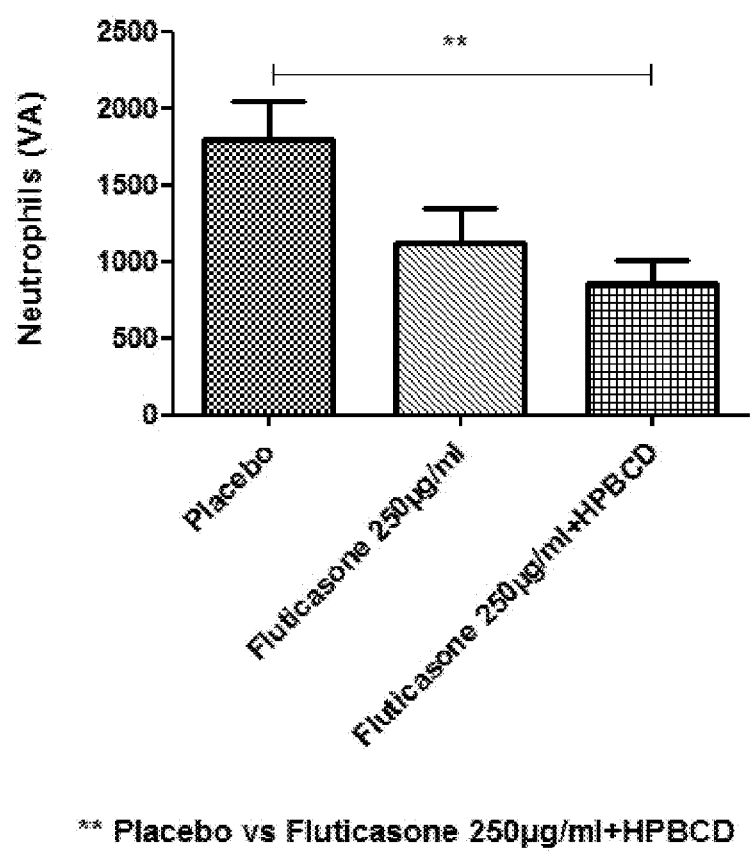
FIG. 21 is a measurement of neutrophil counts in BALF from LPS-exposed animals that are treated with placebo, Fluticasone propionate suspension and hydroxypropyl-beta-cyclodextrin-Fluticasone propionate complex.

The numbers of neutrophils measured in the BALF from experimental animals are surprisingly significantly lowered after treatment with hydroxypropyl-beta-cyclodextrin-Fluticasone propionate complex, about 250 μg/ml, as compared to the placebo-treated animals. For Fluticasone propionate suspension, about 250 μg/ml, the neutrophils number is lowered, as compared to placebo but not significantly. See FIG. 21.

PUBLICATIONS

Frederick G. Vogt and Mark Strohmeier: "2D Solid-State NMR Analysis of Inclusion in Drug-Cyclodextrin Complexes", Molecular Pharmaceutics. 9:3357-3374 (2012).

Agiieros, M., Campanero, M. A., Irache, J. M.: "Simultaneous quantification of different cyclodextrins and Gantrez by HPLC with evaporative light scattering detection", J. Pharm. Biomed. Anal. 39:495-502 (2005).

Thorsteinn Loftsson and Marcus E. Brewster: "Pharmaceutical applications of cyclodextrins: basic science and product development", J. Pharm. Pharmacol. 62:1607-1621 (2010).

Szeman, J., Gerloczy, A., Csabai, K., Szejtli, J., Kis, G. L., Su, P., Chau, R. Y., Jacober, A.: "High-performance liquid chromatographic determination of 2-hydroxypropyl-γ-cyclodextrin in different biological fluids based on cyclodextrin enhanced fluorescence". J. Chromatogr. B. 774: 157-164 (2002).

The complete disclosures of all publications cited herein are incorporated herein by reference in their entireties as if each were individually set forth in full herein and incorporated.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

Having described our inventions, we claim:

1. A method of reducing inflammatory cells in lung tissue in a human wherein the human is in need of such treatment, said method comprising
administering to the human a pharmaceutical composition consisting essentially of budesonide, or a pharmaceutically acceptable salt or ester thereof, and hydroxypropyl-β cyclodextrin (HP-β-CD),
wherein the budesonide, or a pharmaceutically acceptable salt or ester thereof, and the HP-β-CD are in a stoichiometric ratio of from about 1:1 to about 2:1,
wherein the budesonide, or a pharmaceutically acceptable salt or ester thereof, is present in the pharmaceutical composition in an effective amount, and
wherein the effective amount of the budesonide, or a pharmaceutically acceptable salt or ester thereof, is in a range of from about 0.05 mcg to about 1000 mcg.

2. A method of decreasing IL13 in lung tissue in a human wherein the human is in need of such treatment after allergen exposure, said method comprising
administering to the host mammal a pharmaceutical composition consisting essentially of budesonide, or a pharmaceutically acceptable salt or ester thereof, and hydroxypropyl-β cyclodextrin (HP-β-CD),
wherein the budesonide, or a pharmaceutically acceptable salt or ester thereof, and the HP-β-CD are in a stoichiometric ratio of from about 1:1 to about 2:1,
wherein the budesonide, or a pharmaceutically acceptable salt or ester thereof, is present in the pharmaceutical composition in an effective amount, and
wherein the effective amount of the budesonide, or a pharmaceutically acceptable salt or ester thereof, is in a range of from about 0.05 mcg to about 1000 mcg.

3. A method of decreasing bronchial hyper-responsiveness in a human wherein the human is in need of such treatment, said method comprising
administering to the host mammal a pharmaceutical composition consisting essentially of budesonide, or a pharmaceutically acceptable salt or ester thereof, and hydroxypropyl-β cyclodextrin (HP-β-CD),
wherein the budesonide, or a pharmaceutically acceptable salt or ester thereof, and the HP-β-CD are in a stoichiometric ratio of from about 1:1 to about 2:1,
wherein the budesonide, or a pharmaceutically acceptable salt or ester thereof, is present in the pharmaceutical composition in an effective amount, and
wherein the effective amount of the budesonide, or a pharmaceutically acceptable salt or ester thereof, is in a range of from about 0.05 mcg to about 1000 mcg.

4. A method of decreasing IL17 levels in a human wherein the human is in need of such treatment, said method comprising
administering to the host mammal a pharmaceutical composition consisting essentially of budesonide, or a pharmaceutically acceptable salt or ester thereof, and hydroxypropyl-β cyclodextrin (HP-β-CD),
wherein the budesonide, or a pharmaceutically acceptable salt or ester thereof, and the HP-β-CD are in a stoichiometric ratio of from about 1:1 to about 2:1,
wherein the budesonide, or a pharmaceutically acceptable salt or ester thereof, is present in the pharmaceutical composition in an effective amount, and
wherein the effective amount of the budesonide, or a pharmaceutically acceptable salt or ester thereof, is in a range of from about 0.05 mcg to about 1000 mcg.

5. A method of decreasing CXCL-1 levels in a human wherein the human is in need of such treatment, said method comprising
administering to the host mammal a pharmaceutical composition consisting essentially of budesonide, or a pharmaceutically acceptable salt or ester thereof, and hydroxypropyl-β cyclodextrin (HP-β-CD),
wherein the budesonide, or a pharmaceutically acceptable salt or ester thereof, and the HP-β-CD are in a stoichiometric ratio of from about 1:1 to about 2:1,
wherein the budesonide, or a pharmaceutically acceptable salt or ester thereof, is present in the pharmaceutical composition in an effective amount, and wherein the effective amount of the budesonide, or a pharmaceutically acceptable salt or ester thereof, is in a range of from about 0.05 mcg to about 1000 mcg.

6. A method of decreasing neutrophils in lung tissue in a human, wherein the human is in need of such treatment after cigarette smoke exposure, said method comprising
administering to the host mammal a pharmaceutical composition consisting essentially of budesonide, or a pharmaceutically acceptable salt or ester thereof, and hydroxypropyl-β cyclodextrin (HP-β-CD),
wherein the budesonide, or a pharmaceutically acceptable salt or ester thereof, and the HP-β-CD are in a stoichiometric ratio of from about 1:1 to about 2:1,
wherein the budesonide, or a pharmaceutically acceptable salt or ester thereof, is present in the pharmaceutical composition in an effective amount, and
wherein the effective amount of the budesonide, or a pharmaceutically acceptable salt or ester thereof, is in a range of from about 0.05 mcg to about 1000 mcg.

7. The method of claim 1, wherein the pharmaceutical composition is an inhalation solution.

8. The method of claim 2, wherein the pharmaceutical composition is an inhalation solution.

9. The method of claim 3, wherein the pharmaceutical composition is an inhalation solution.

10. The method of claim 4, wherein the pharmaceutical composition is an inhalation solution.

11. The method of claim 5, wherein the pharmaceutical composition is an inhalation solution.

12. The method of claim 6, wherein the pharmaceutical composition is an inhalation solution.

13. The method of claim 1, wherein the pharmaceutical composition is a pharmaceutical powder.

14. The method of claim 2, wherein the pharmaceutical composition is a pharmaceutical powder.

15. The method of claim 3, wherein the pharmaceutical composition is a pharmaceutical powder.

16. The method of claim 4, wherein the pharmaceutical composition is a pharmaceutical powder.

17. The method of claim 5, wherein the pharmaceutical composition is a pharmaceutical powder.

18. The method of claim 6, wherein the pharmaceutical composition is a pharmaceutical powder.

19. The method of claim 1, wherein said administration delivers to the patient a molecular dose of the budesonide, or a pharmaceutically acceptable salt or ester thereof, in a range of from about 0.1 to about 500 mcg.

20. The method of claim 2, wherein said administration delivers to the patient a molecular dose of the budesonide, or a pharmaceutically acceptable salt or ester thereof, in a range of from about 0.1 to about 500 mcg.

21. The method of claim 3, wherein said administration delivers to the patient a molecular dose of the budesonide, or a pharmaceutically acceptable salt or ester thereof, in a range of from about 0.1 to about 500 mcg.

22. The method of claim 4, wherein said administration delivers to the patient a molecular dose of the budesonide, or a pharmaceutically acceptable salt or ester thereof, in a range of from about 0.1 to about 500 mcg.

23. The method of claim 5, wherein said administration delivers to the patient a molecular dose of the budesonide, or a pharmaceutically acceptable salt or ester thereof, in a range of from about 0.1 to about 500 mcg.

24. The method of claim 6, wherein said administration delivers to the patient a molecular dose of the budesonide, or a pharmaceutically acceptable salt or ester thereof, in a range of from about 0.1 to about 500 mcg.

25. The method of 1, wherein said administration delivers to the patient a molecular dose of the budesonide, or a pharmaceutically acceptable salt or ester thereof, in a range of from about 40 to about 200 mcg per day in accordance with the prescribed treatment regimen.

26. The method of 2, wherein said administration delivers to the patient a molecular dose of the budesonide, or a pharmaceutically acceptable salt or ester thereof, in a range of from about 40 to about 200 mcg per day in accordance with the prescribed treatment regimen.

27. The method of 3, wherein said administration delivers to the patient a molecular dose of the budesonide, or a pharmaceutically acceptable salt or ester thereof, in a range of from about 40 to about 200 mcg per day in accordance with the prescribed treatment regimen.

28. The method of 4, wherein said administration delivers to the patient a molecular dose of the budesonide, or a pharmaceutically acceptable salt or ester thereof, in a range of from about 40 to about 200 mcg per day in accordance with the prescribed treatment regimen.

29. The method of 5, wherein said administration delivers to the patient a molecular dose of the budesonide, or a pharmaceutically acceptable salt or ester thereof, in a range of from about 40 to about 200 mcg per day in accordance with the prescribed treatment regimen.

30. The method of 6, wherein said administration delivers to the patient a molecular dose of the budesonide, or a pharmaceutically acceptable salt or ester thereof, in a range of from about 50 to about 200 mcg per day in accordance with the prescribed treatment regimen.

* * * * *